US010100274B2

(12) United States Patent
Taniguchi et al.

(10) Patent No.: US 10,100,274 B2
(45) Date of Patent: Oct. 16, 2018

(54) METHOD FOR PREPARING CHONDROCYTES

(71) Applicant: PUBLIC UNIVERSITY CORPORATION YOKOHAMA CITY UNIVERSITY, Yokohama-shi, Kanagawa (JP)

(72) Inventors: Hideki Taniguchi, Yokohama (JP); Takanori Takebe, Yokohama (JP); Shinji Kobayashi, Yokohama (JP)

(73) Assignee: PUBLIC UNIVERSITY CORPORATION YOKOHAMA CITY UNIVERSITY, Yokohama-Shi, Kanagawa (JP)

( * ) Notice: Subject to any disclaimer, the term of this patent is extended or adjusted under 35 U.S.C. 154(b) by 72 days.

(21) Appl. No.: 14/778,700

(22) PCT Filed: Mar. 20, 2014

(86) PCT No.: PCT/JP2014/057673
§ 371 (c)(1),
(2) Date: Sep. 21, 2015

(87) PCT Pub. No.: WO2014/148592
PCT Pub. Date: Sep. 25, 2014

(65) Prior Publication Data
US 2016/0046903 A1 Feb. 18, 2016

(30) Foreign Application Priority Data

Mar. 21, 2013 (JP) ................................. 2013-058534

(51) Int. Cl.
| C12N 5/077 | (2010.01) |
| C12N 5/078 | (2010.01) |
| A61L 27/38 | (2006.01) |
| C12N 5/00  | (2006.01) |
| A61K 35/32 | (2015.01) |
| A61L 27/36 | (2006.01) |
| G01N 33/50 | (2006.01) |

(52) U.S. Cl.
CPC ............ *C12N 5/0062* (2013.01); *A61K 35/32* (2013.01); *A61L 27/3612* (2013.01); *A61L 27/3808* (2013.01); *A61L 27/3817* (2013.01); *C12N 5/0655* (2013.01); *G01N 33/5082* (2013.01); *A61L 2430/06* (2013.01); *A61L 2430/10* (2013.01); *C12N 2501/105* (2013.01); *C12N 2501/11* (2013.01); *C12N 2501/113* (2013.01); *C12N 2501/115* (2013.01); *C12N 2501/119* (2013.01); *C12N 2501/12* (2013.01); *C12N 2501/15* (2013.01); *C12N 2501/155* (2013.01); *C12N 2501/165* (2013.01); *C12N 2501/39* (2013.01); *C12N 2502/28* (2013.01); *C12N 2513/00* (2013.01)

(58) Field of Classification Search
CPC ........ C12N 2502/1317; C12N 2502/28; C12N 5/069; C12N 5/0692; C12N 5/0655; C12N 5/0662; C12N 2502/1352
See application file for complete search history.

(56) References Cited

U.S. PATENT DOCUMENTS

| 2003/0180943 A1 | 9/2003 | Yanaga |
| 2009/0317448 A1 | 12/2009 | Bonassar et al. |
| 2009/0324560 A1 | 12/2009 | Taniguchi et al. |

FOREIGN PATENT DOCUMENTS

| JP | 2012-031127 A | 2/2012 |
| WO | WO 02/12451 A1 | 2/2002 |
| WO | WO 2004/039248 A2 | 5/2004 |
| WO | WO 2008/091013 A1 | 7/2008 |

OTHER PUBLICATIONS

Trkov et al., Micropatterned 3-dimensional hydrogel system to study human endothelial-mesenchymal stem cell interactions. Journal of Tissue Engineering & Regenerative Medicine, vol. 4, No. 3 (2011) pp. 205-215.*
Duong et al., Modulation of 3D fibrin matrix stiffness by intrinsic fibrinogen-thrombin compositions and by extrinsic cellular activity. Tissue Engineering Part A vol. 15, No. 7 (2009) pp. 1865-1876.*
Saleh et al., Effects of endothelial cells on human mesenchymal stem cell activity in a three-dimensional in vitro model. European Cells and Materials, vol. 22 (2011) pp. 242-257.*
Dulbecco's Modified Eagle Medium (DME) Formulation. Datasheet [online]. Sigma-Aldrich, 2017 [retrieved on Mar. 3, 2017]. Retrieved from the Internet: <URL: http://www.sigmaaldrich.com/life-science/cell-culture/learning-center/media-formulations/dme.html>.*
Price et al., Relationship between in vitro growth promotion and biophysical and biochemical properties of the serum supplement. In Vitro vol. 18, No. 6 (1982) pp. 576-584.*

(Continued)

Primary Examiner — Kara D Johnson
(74) *Attorney, Agent, or Firm* — Birch, Stewart, Kolasch & Birch, LLP

(57) ABSTRACT

The present invention provides a method for preparing chondrocytes which enable construction of a cartilage tissue, the method being capable of solving the problems with conventional methods.
A method for preparing chondrocytes, comprising co-culturing chondrogenic cells with vascular cells. A composition for cartilage regenerative therapy, comprising chondrocytes prepared by the above-described method. A method of screening for drugs effective as pharmaceuticals, comprising using chondrocytes prepared by the above-described method, a cartilage tissue formed from the chondrocytes and/or cells derived from the cartilage tissue. A method for preparing a matrix produced by chondrocytes, comprising using chondrocytes prepared by the above-described method, a cartilage tissue formed from the chondrocytes and/or cells derived from the cartilage tissue. A method for cartilage regeneration, comprising transplanting chondrocytes prepared by the above-described method into an organism to form a cartilage tissue.

20 Claims, 15 Drawing Sheets
(15 of 15 Drawing Sheet(s) Filed in Color)

(56) References Cited

OTHER PUBLICATIONS

Growth Factors in Thermo Scientific HyClone Cell Culture Serum. Datasheet [online]. Thermo Scientific, 2007 [retrieved on Mar. 3, 2017]. Retrieved from the Internet: <URL: http://www.stemcell.so/images/upload/pdf/528ed1a462859.pdf>.*
Yang et al., Coculture-driven mesenchymal stem cell-differentiated articular chondrocyte-like cells support neocartilage development. Stem Cells Translational Medicine, vol. 1, No. 11 (2012) pp. 843-854.*
Oswald et al., Mesenchymal stem cells can be differentiated into endothelial cells in vitro. Stem Cells, vol. 22, No. 3 (2004) pp. 3777-384.*
English translation of International Preliminary Report on Patentability dated Sep. 21, 2015, in PCT International Application No. PCT/JP2014/057673.
Bittner et al., "Role of the Subchondral Vascular System in Endochondral Ossification: Endothelial Cells Specifically Derepress Late Differentiation in Resting Chondrocytes in Vitro", Experimental Cell Research, vol. 238, Article No. EX973849, 1998, pp. 491-497.
Hendriks et al., "Co-culture in cartilage tissue engineering", Journal of Tissue Engineering and Regenerative Medicine, vol. 1, 2007, pp. 170-178.

International Search Report issued in PCT/JP2014/057673, dated Jun. 17, 2014.
Sayed et al., "Stimulated Chondrogenesis via Chondrocytes Co-culturing", Journal of Biochips & Tissue Chips, vol. S2, 2012, pp. 1-11.
Written Opinion issued in PCT/JP2014/057673, dated Jun. 17, 2014.
Aguirre et al, "Dynamics of bone marrow-derived endothelial progenitor cell/mesenchymal stem cell interaction . . . ," Biochemical and Biophysical Research Communications, Orlando, FL, vol. 400, No. 2, Sep. 17, 2010, (Available online Aug. 21, 2010), pp. 284-291, XP027288473.
Extended European Search Report, dated Oct. 7, 2016, for European Application No. 14769212.3.
Prestwich et al, "Evaluating Drug Efficacy and Toxicology in Three Dimensions: Using Synthetic Extracellular Matrices in Drug Discovery," Accounts of chemical research, vol. 41, No. 1, Jan. 1, 2008, (Published on the Web Jul. 27, 2007), pp. 139-148, XP009169219.
Walles et al., "Experimental generation of a tissue-engineered functional and vascularized trachea," Journal of Thoracic and Cardiovascular Surgery, Mosby-Year Book Inc., St. Louis, MO, vol. 128, No. 6, Dec. 1, 2004, pp. 900-906, XP004661340.

* cited by examiner

A.

B.

Characteristics of human cartilage progenitor cell

Kobayashi S, Takebe T, et al. *PLoS ONE*, 2011, *PNAS* 108, 14479-14484, 2011
Method for preparing chondrocytes   Japanese Patent No. 4748222
(PCT/JP2008/051327)

A.

B.

A.

B.

Perichondrocytes (3x10⁶) + Vascular endothelial cells (1x10⁶)    ⇑ Conventional culture dish 3-D tissue, approx. 400 μm, prepared in the plate shown in the left panel.

A

B (✕ = Not formed.)

METHOD FOR PREPARING CHONDROCYTES

TECHNICAL FIELD

The present invention relates to a method for preparing chondrocytes.

BACKGROUND ART

When human cartilage tissue is congenitally deficient or becomes damaged or deficient in the course of lifetime, usually the cartilage tissue is not regenerated. For treating diseases of such human cartilage, a method has been used in which a cartilage tissue is taken from a site of a patient and transplanted into the deficient site of the patient. However, this method has a problem that the donor site is highly damaged and the amounts of the tissue that can be taken are limited. Then, the present inventors have developed a method in which a part of autologous perichondrium-derived chondrogenic cells is collected, cultured ex vivo for expansion and subsequently differentiated into chondrocytes in planar culture by adding a differentiation-inducing factor such as cytokine (Patent Document No. 1 and Non-Patent Document No. 1).

On the other hand, as a means to prepare a three-dimensional cartilage tissue for restoring cartilage tissue, a method is known in which a grafting material is formed by filling a carrier (such as porous, biocompatible scaffold material) with cultured chondrogenic cells or by allowing the cells to adhere to the carrier (Patent Documents Nos. 2-5).

PRIOR ART LITERATURE

Patent Documents

Patent Document No. 1: Japanese Patent No. 4748222
Patent Document No. 2: Japanese Unexamined Patent Publication No. 2012-000262
Patent Document No. 3: Japanese Unexamined Patent Publication No. 2011-078710
Patent Document No. 4: Japanese Unexamined Patent Publication No. 2009-226221
Patent Document No. 5: Japanese Unexamined Patent Publication No. 2009-106214

Non-Patent Documents

Non-Patent Document No. 1: Kobayashi et al., Proc. Natl. Acad. Sci. USA 108:14479-14484, 2011

DISCLOSURE OF THE INVENTION

Problem for Solution by the Invention

The method of inducing differentiation into chondrocytes using a differentiation-inducing factor such as cytokine in planar culture had the following problems.
1. Costs of reagents necessary for differentiation induction are high; and huge expenses are required for differentiation induction.
2. Since a long period (two to four months) of culture is needed until differentiation induction into chondrocytes, risks for clinical application (such as tumorigenesis) increase.
3. Differentiation-induced chondrocytes are in a state of gel, which makes it extremely difficult to control the morphology of the cells at the time of transplantation.

The method of reconstructing a three-dimensional cartilage tissue using a carrier had the following problems.
1. Since the carrier is a foreign substance to organisms, there occur infection, inflammation, and scar tissue formation resulting therefrom
2. Appropriate process of differentiation into chondrocytes is not recapitulated because chondrogenic cells are filled in or adhered to the carrier.
3. Since the induction efficiency of differentiation into terminally differentiated chondrocytes is low, it is difficult to obtain homogeneous and quantitatively sufficient three-dimensional cartilage tissue.

It is therefore an object of the present invention to provide a method for preparing chondrocytes, which enables construction of cartilage tissue in a way that can resolve the above-described problems.

Means to Solve the Problem

Since blood vessels are not present in adult cartilage tissue, blood vessels have been believed unnecessary in the development concept of conventional cartilage regenerative therapy. However, the present inventors have found the following: in early stages of cartilage development, it is important that transient vascularization should occur and chondrogenic cells take an orderly spatial arrangement with vascular cells; as a result, orchestration occurs in the interaction with vascular endothelial cells, inducing the proliferation and differentiation of chondrogenic cells; and finally, an avascular cartilage tissue is formed.

Then, the present inventors have established a three-dimensional culture system which recapitulates the interactions between chondrogenic cells and vascular endothelial cells that have not attracted researchers' attention at all. When transplanted into organisms, the three-dimensional tissue induced in this system was capable of constructing an elastic cartilage more efficiently than the conventional method (pellet transplantation). The technique attempting at three-dimensional reconstruction of cartilage tissue by focusing on the intercellular interactions between chondrogenic cells and vascular cells (e.g., vascular endothelial cells) has not existed to date and is a method that features extremely high novelty.

A summary of the present invention is as described below.
(1) A method for preparing chondrocytes, comprising co-culturing chondrogenic cells with vascular cells.
(2) The method of (1) above, wherein the chondrogenic cells amplify as a result of co-culture with vascular cells.
(3) The method of (1) or (2) above, wherein three-dimensional tissues are formed by co-culturing chondrogenic cells with vascular cells on a support.
(4) The method of (3) above, wherein the support is a substrate with a hardness of 0.5-25 kPa.
(5) The method of (1) or (2) above, wherein three-dimensional tissues are formed by co-culturing chondrogenic cells with vascular cells on a plate having a shape in which cells gather in the bottom.
(6) The method of any one of (1) to (5) above, wherein chondrogenic cells are co-cultured with vascular cells in the presence of at least one component selected from the group consisting of fibroblast growth factor 2 (bFGF (FGF2)), fibroblast growth factor 4 (FGF4), fibroblast growth factor 5 (FGF5), bone morphogenetic protein 2 (BMP2), bone morphogenetic protein 3 (BMP3), bone morphogenetic protein 4 (BMP4), bone morphogenetic protein 6 (BMP6), connective tissue growth factor (CTGF), transforming growth factor β1 (TGF-β1), transforming growth factor β2 (TGF-β2), transforming growth factor β3 (TGF-β3), insulin-like growth factor 1 (IGF-1), hepatocyte growth factor (HGF), aggrecan, hyaluronic acid, endothelial cell growth factor (ECGF), endothelial cell growth supplement (ECGS), endothelial cell-derived growth factor (ECDGF), epidermal growth factor (EGF), acidic fibroblast growth factor (acidic FGF), macrophage-derived growth factor (MDGF), platelet-derived growth factor (PDGF), tumor angiogenesis factor (TAF), vascular endothelial growth factor (VEGF), bovine brain extract (BBE), bovine pituitary extract (BPE), glucocorticoid, cholesterol, and vitamins.

(7) The method of any one of (1) to (6) above, wherein chondrogenic cells and vascular cells are co-cultured at a mixing ratio of 1:0.3-1.

(8) The method of any one of (1) to (7) above, wherein the chondrogenic cell is any one of chondrocyte, immature chondrocyte, cartilage progenitor cell or cartilage stem cell.

(9) The method of (8) above, wherein the chondrocyte has been obtained from a tissue selected from the group consisting of rib cartilage, nasal cartilage, ear cartilage, tracheal cartilage, pharyngeal cartilage, thyroid cartilage, arytenoid cartilage, cricoid cartilage, tendon, ligament, interarticular cartilage, and intervertebral disc.

(10) The method of (8) above, wherein the immature chondrocyte, the cartilage progenitor cell or the cartilage stem cell has been obtained from a tissue selected from the group consisting of cartilage, perichondrium, bone marrow, placenta, umbilical cord, skin, muscle, fat, and periosteum

(11) The method of any one of (1) to (10) above, wherein the chondrogenic cell and the vascular cell are derived from the same individual.

(12) The method of any one of (1) to (10) above, wherein the chondrogenic cell and the vascular cell are derived from different individuals.

(13) A composition for use in cartilage regenerative therapy, comprising chondrocytes prepared by the method of any one of (1) to (12).

(14) The composition of (13) above, which is used for transplantation into an organism to induce the formation of a cartilage tissue.

(15) The composition of (14) above, wherein a vascular network is constructed upon transplantation into an organism.

(16) The composition of (15) above, wherein vascular perfusion occurs in the vascular network.

(17) The composition of (16) above, wherein the vascular network once constructed disappears to result in the formation of an avascular cartilage tissue.

(18) A method of screening for drugs effective as pharmaceuticals, comprising using chondrocytes prepared by the method of any one of (1) to (12) above, a cartilage tissue formed from the chondrocytes and/or cells derived from the cartilage tissue.

(19) A method for preparing a matrix produced by chondrocytes, comprising using chondrocytes prepared by the method of any one of (1) to (12) above, a cartilage tissue formed from the chondrocytes and/or cells derived from the cartilage tissue.

(20) A method for cartilage regeneration, comprising transplanting chondrocytes prepared by the method of any one of (1) to (12) above into an organism to form a cartilage tissue.

Effect of the Invention

1. When linked with already developed techniques for manipulating perichondrium-derived stem cells (e.g., Japanese Patent No. 4748222), the present invention will be a useful technique for mass creation of high quality three-dimensional cartilage.

2. Induction factors necessary for differentiation induction (such as cytokine) can be decreased, which leads to huge cost reduction.

3. It is possible to shorten the culture period required for inducing differentiation of chondrogenic cells.

4. Since three-dimensional tissues with a certain degree of mechanical strength are formed during culture, it becomes possible to transplant the tissues with their shape kept intact immediately after transplantation. This makes it possible to predict, to some extent, the shape of the three-dimensional tissues after transplantation.

5. Since the engraftment efficiency of chondrogenic cells and the efficiency of inducing them to terminal differentiation are high, a small number of cells are sufficient for efficient formation of three-dimensional tissues.

6. Since scaffold materials such as high molecular weight polymers are not necessary, inflammation or absorption does not occur.

The present specification encompasses the contents disclosed in the specification and/or the drawings of Japanese Patent Application No. 2013-58534 based on which the present patent application claims priority.

BRIEF DESCRIPTION OF THE DRAWINGS

The patent or application file contains at least one color drawing. Copies of this patent or patent application publication with color drawing will be provided by the USPTO upon request and payment of the necessary fee.

B) Human cartilage progenitor cells (hereinafter, frequently abbreviated to "CPCs") were shown to express $CD44^+$ and $CD90^+$ markers; had high proliferative capacity and pluripotency, two characteristic features of progenitor cells; and reconstructed human elastic cartilage tissues for a long period upon transplantation.

Figure 1:
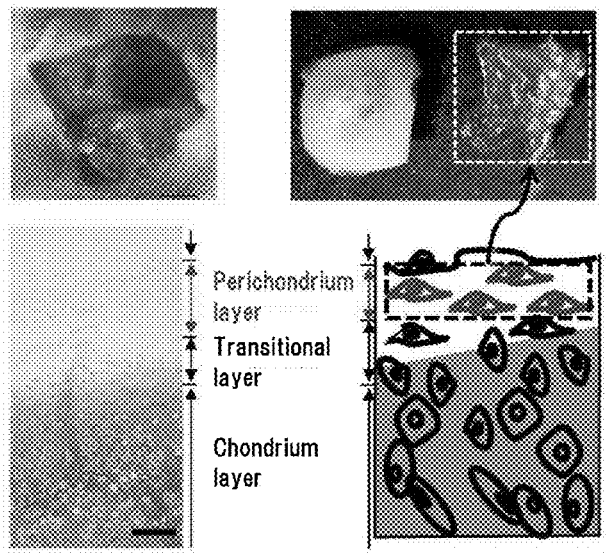
FIG. 1 Identification of Cartilage Progenitor Cells Present in Human Ear Perichondrium A) Residual ear cartilage removed from a microtia patient was separated into perichondrium layer and cartilage layer.
Figure 1:
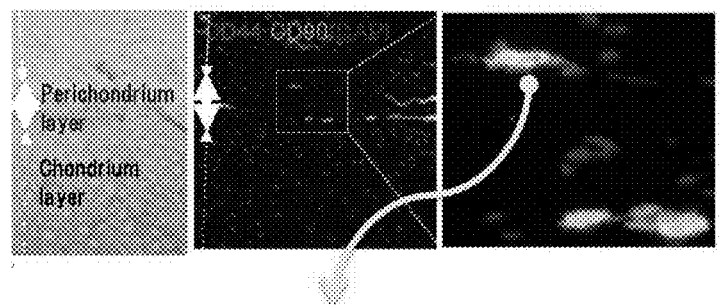
Figure 1:
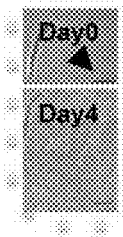
Figure 1:
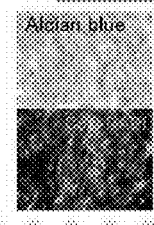
Figure 1:
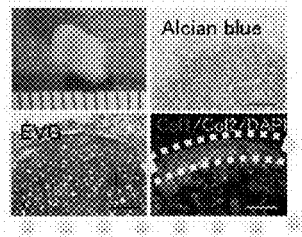
Figure 2:
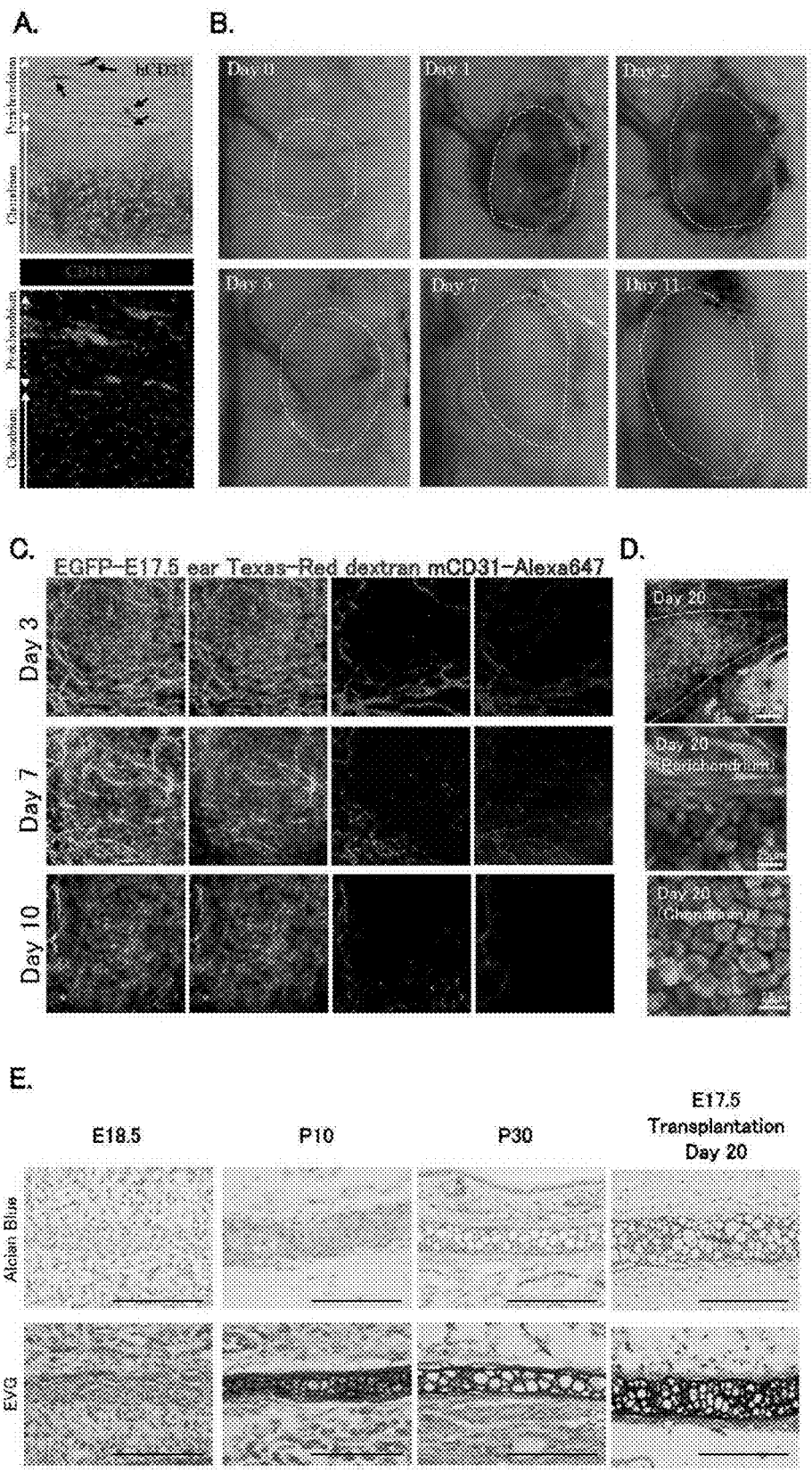

FIG. 2 Intravital Tracking the Process of Chondrogenesis by Cranial Window Method A) Vascular endothelial cells were present in the perichondrium layer of human ear cartilage.

B) Gross observations of ear cartilage of E17.5 EGFG transgenic mice transplanted into cranial windows C) Periodical observation of the same field with confocal microscope Tetramethylrhodamine-conjugated dextran and Alexa647-conjugated mouse specific CD31 (mCD31) antibody were injected into the tail vein of mice to visualize the vascular endothelial cells and the blood flow of the mice. At day 3 of transplantation, it was confirmed that blood vessels with blood flow had invaded into the transplant. These blood vessels regressed at day 10 of transplantation (scale bar: 75 µm).

D) At day 20 of transplantation, perichondral tissues having blood vessels encapsulating cartilage tissues were formed. Cells constituting the cartilage tissues presented cobblestone-like shapes.

E) It was observed that the ear cartilage tissues of E17.5 EGFP transgenic mice formed a mature elastic cartilage in the same manner as the ear cartilage tissues at developmental stages P10 and P30 (scale bar: 100 µm).

Figure 3:
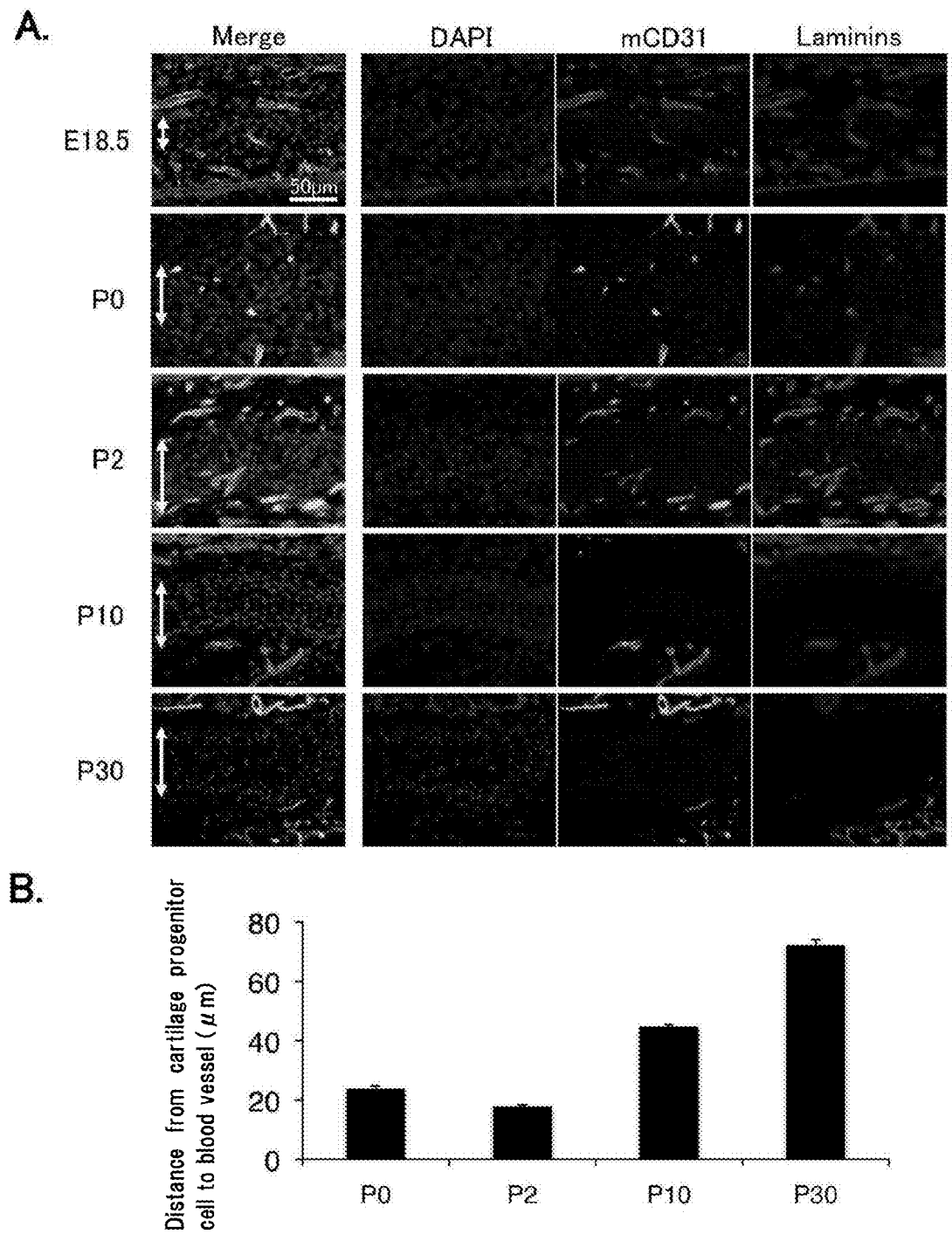

FIG. 3 Transient Vascularization in Mouse Ear Cartilage at Early Developmental Stages A) Immunohistochemical staining was performed on ear cartilages at developmental stages from E18.5 to P30 with mCD31 (green) and laminins (red) (Double-headed arrows indicate the cartilage layer; scale bar: 50 μm). The largest number of endothelial cells were confirmed at stage P2, while no endothelial cell was observed at stage P30.

B) Average distance between CPCs and vessels closest thereto was determined and it measured the shortest (17.8 μm) at postnatal day 2. Data are shown as the mean±s.d. obtained from at least three independent specimens (more than 200 cells were measured).

Figure 4:
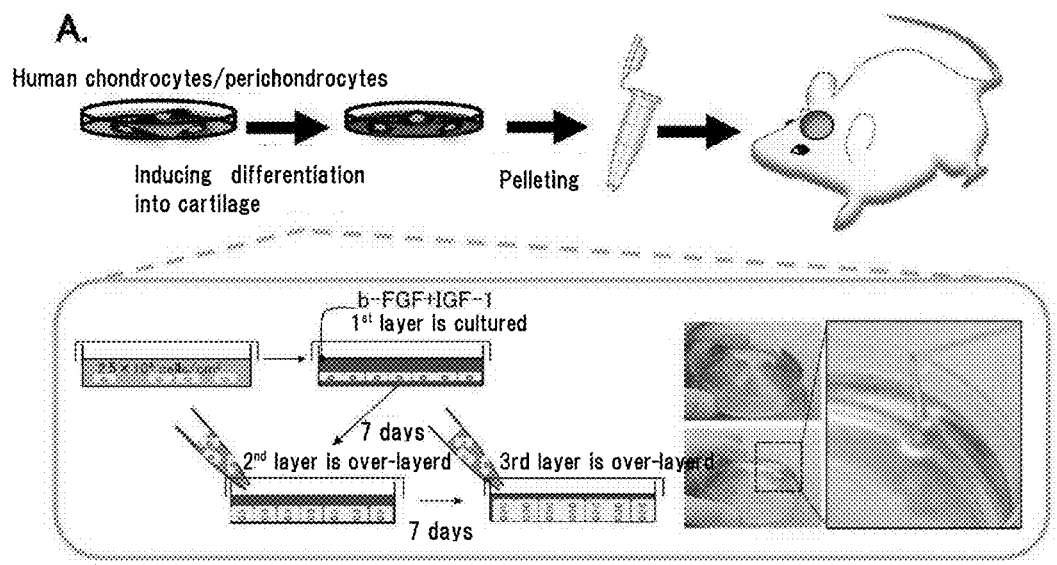
Figure 4:
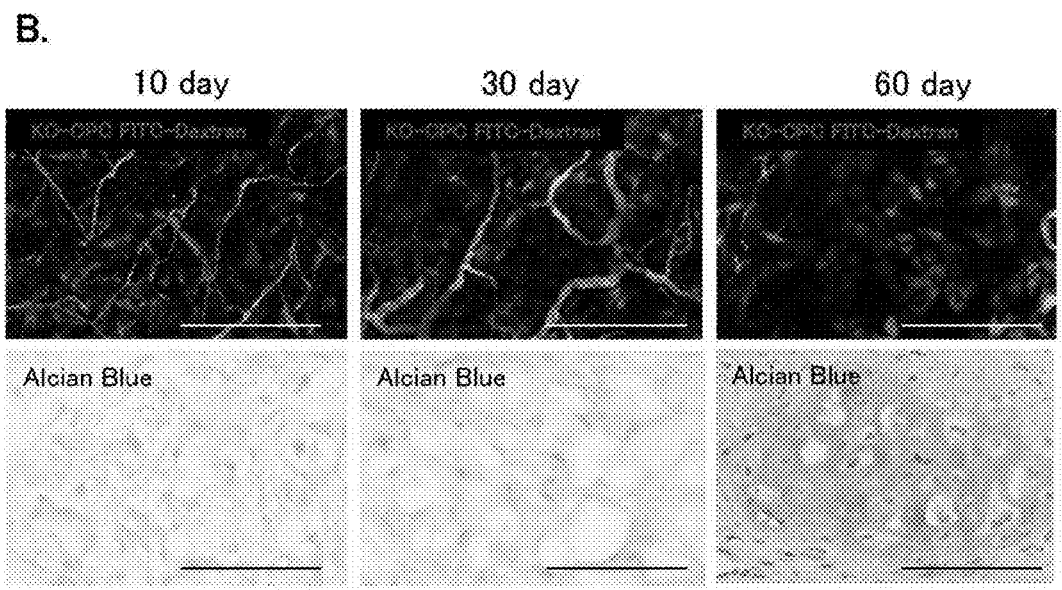

FIG. 4 Transient Vascularization in the Process of Reconstruction of Human Cartilage A) CPCs which had been subjected to the conventional cartilage differentiation induction method were transplanted into cranial windows.

B) Blood perfusion was confirmed by live imaging at days 10 and 30 of transplantation. At day 60 of transplantation, blood vessels regressed. Mature cartilage layer was confirmed by Alcian Blue staining (scale bar: 100 μm).

Figure 5:
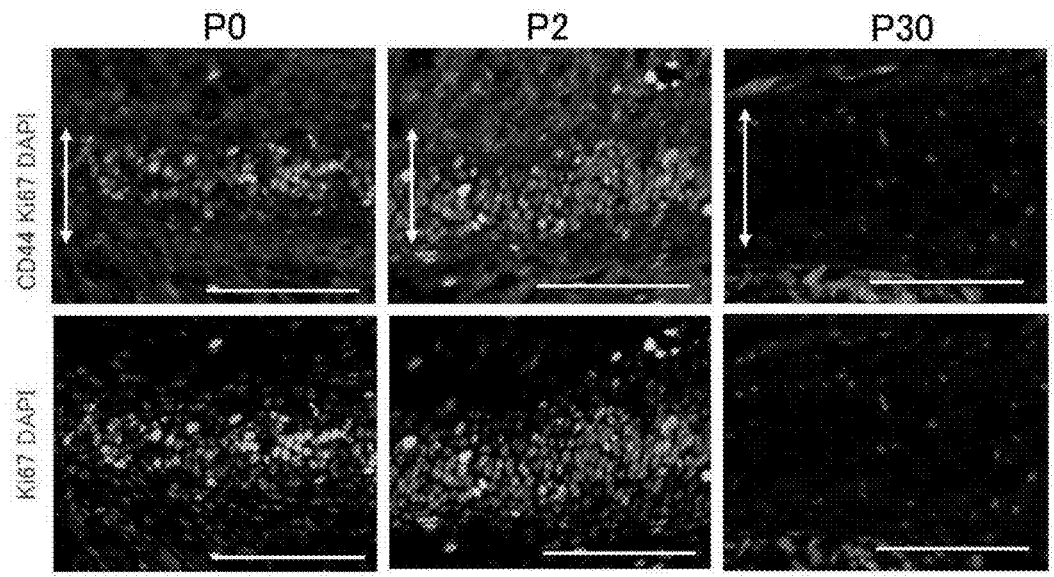
Figure 5:
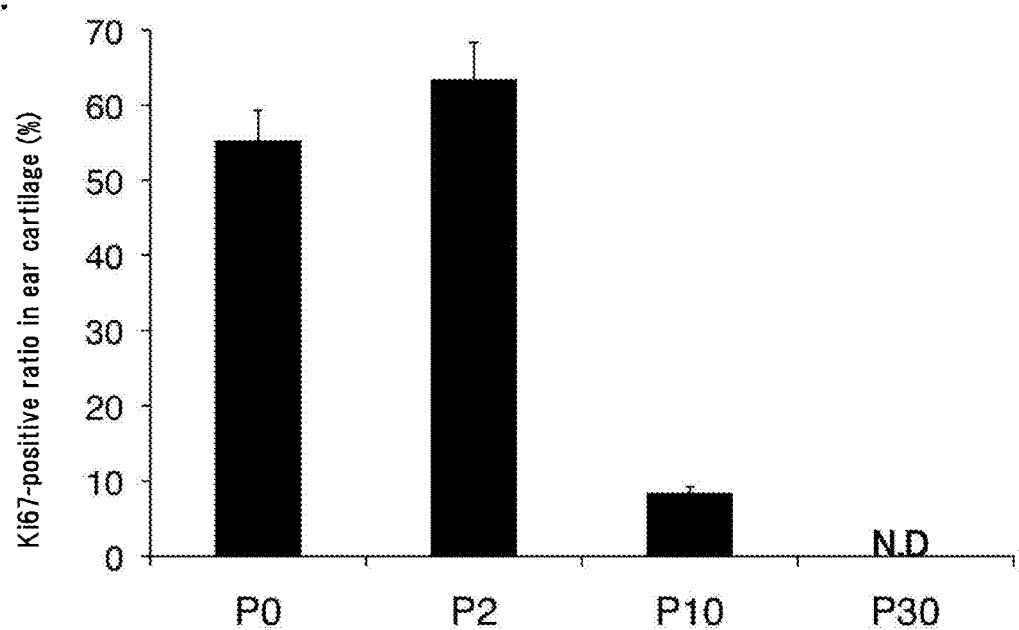

FIG. 5 Marked proliferation of CPCs in Ear Cartilage at Early Developmental Stages A) In ear cartilage at developmental stages P0, P10 and P30, proliferation of CD44-positive CPCs was confirmed with Ki67. At stages P0 and P2, CPCs had proliferated more extensively. On the other hand, Ki67-positive cells were not observed at stage P30 (scale bar: 100 μm, N.D.: not detected).

B) The number of Ki67-positive, proliferating cells in cartilage layer was quantitatively determined. Data are shown as the mean±s.d. obtained from at least five independent specimens.

Figure 6:
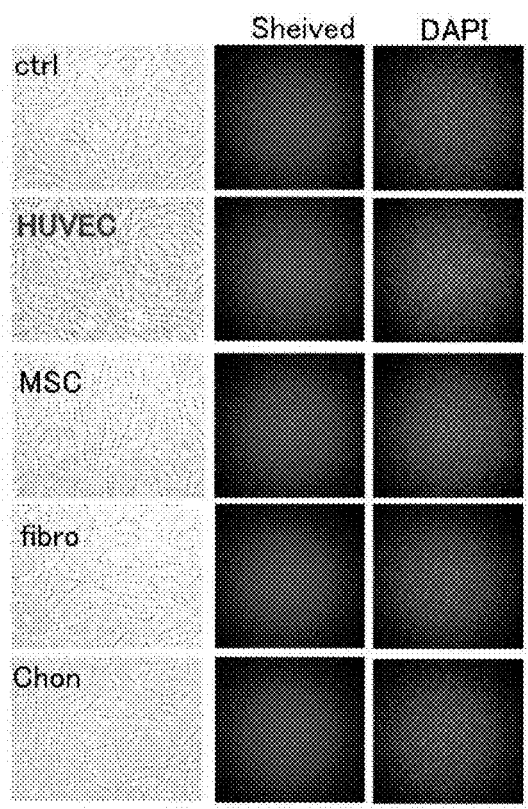
Figure 6:
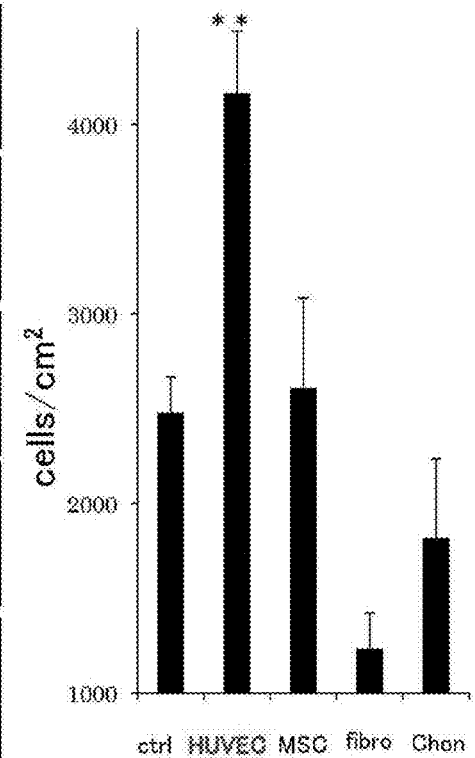
Figure 6:
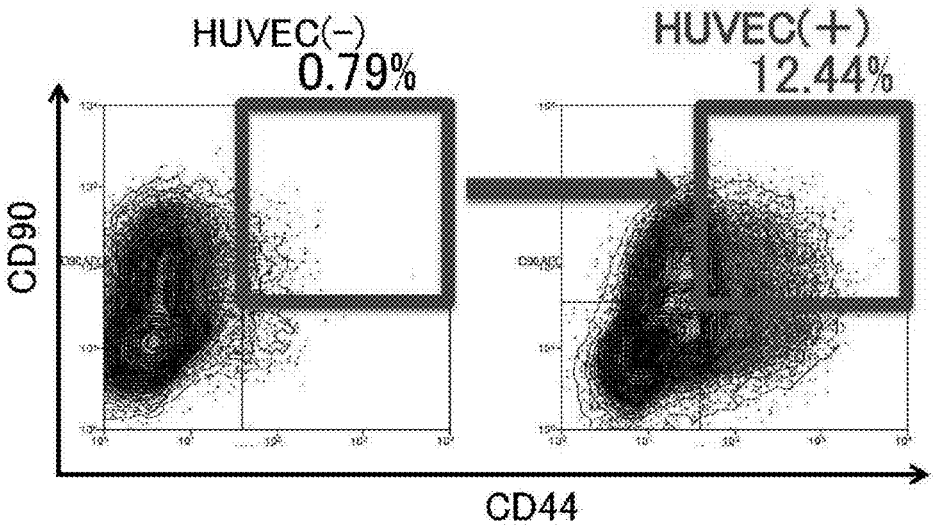

FIG. 6 Enhanced Proliferation of CPCs in vitro by Co-culture with Vascular Endothelial Cells A) CPCs were seeded at a low density and co-cultured with human umbilical vein endothelial cells by transwell assay. As a result, CPCs proliferated in a manner specific for vascular endothelial cells. Cell count per unit area was quantified at day 11 of co-culture and thereafter. Data are shown as the mean±s.d. obtained from at least independent specimens (N=5; **: P<0.01; Ctrl: Control; HUVEC: Normal Human Umbilical Vascular Endothelial Cells; MSC: mesenchymal stem cells; Fibro: dermal fibroblasts; Chon: chondrocytes).

B) Expression of cell surface markers CD44+ and CD90+ present in human CPCs was analyzed by flow cytometry.

Figure 7:
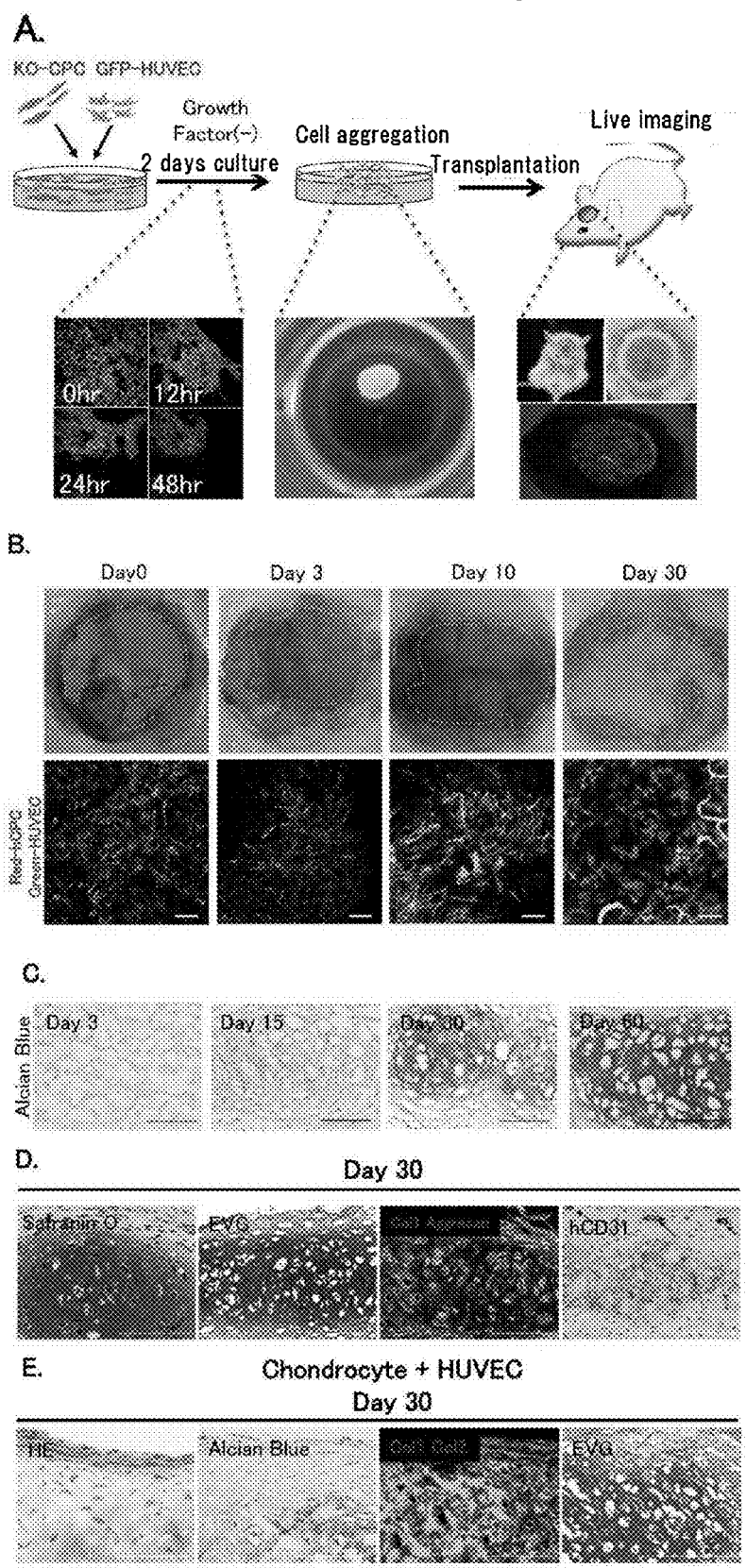

FIG. 7 Autonomous Formation of Three-Dimensional Tissues in Human CPCs by Co-culture with Vascular Endothelial Cells A) Development of a novel three-dimensional culture system by recapitulating early processes of cartilage development. Human CPCs self-organized into three-dimensional tissues in vitro without using scaffold materials or growth factors. (green: Normal Human Umbilical Vascular Endothelial Cells: HUVEC; red: human cartilage progenitor cells: hCPCs)

B) Chronological observation in vivo of CPCs co-cultured with HUVEC. Gross observation (upper panel), live imaging (lower panel) (scale bar: 100 μm). Vascular invasion occurred shortly after transplantation, followed by vascular regression.

C) Alcian Blue staining at days 3, 15, 30 and 60 after transplantation of CPCs co-cultured with HUVEC (scale bar: 200 μm).

D) Safranin O (leftmost image) and Elastica Van Gieson (second image from the left) staining revealed that CPCs co-cultured with HUVEC formed an elastic cartilage tissue upon transplantation. Further, immunohistochemical staining (second image from the right) with aggrecan (green) and collagen I (red) revealed that the cells formed both perichondrium layer and cartilage layer. Immunohistochemical staining of hCD31 (rightmost image) showed the presence of endothelial cells in the perichondrium layer. (scale bar: 100 μm)

E) Dedifferentiated chondrocytes and HUVEC were co-cultured using a similar three-dimensional culture system. Alcian Blue (second image from the left) and Elastica Van Gieson (rightmost image) staining confirmed that an elastic cartilage tissue was formed. (scale bar: 100 μm)

Figure 8:
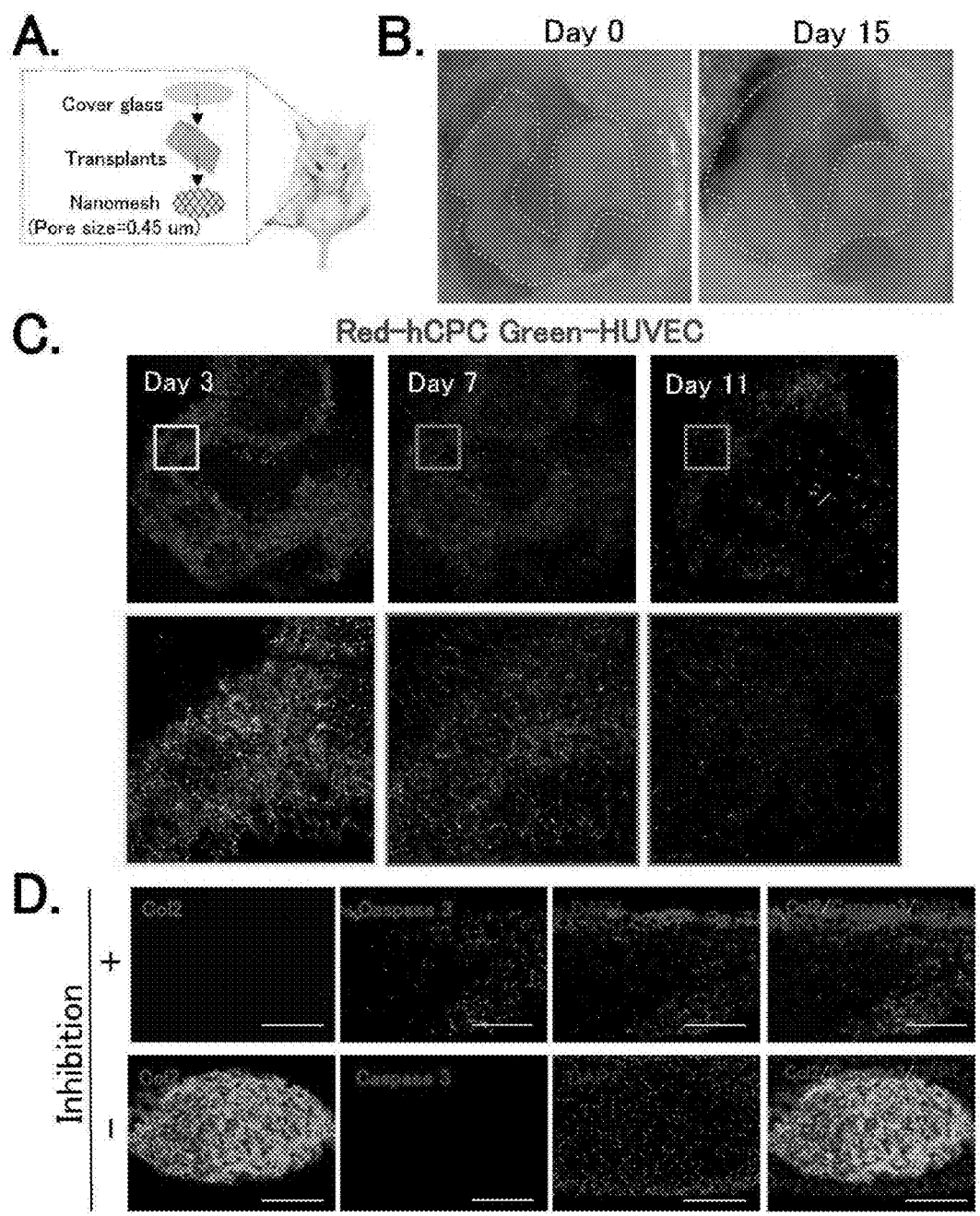

FIG. 8 Inhibition of Human Elastic Cartilage Formation Using Blood Flow-Inhibited Transplant Model A) Scheme for preparing a blood flow-inhibited transplant model. CPCs co-cultured with HUVEC and transplanted into a cranial window were sandwiched between a cover glass and a nanomesh (0.45 μm in pore size) so that the host blood flow would not act on the transplant.

B) Gross observations from day 0 to day 15 of transplantation showed that blood perfusion into the transplant was completely inhibited.

C) Observation by live imaging confirmed a failing engraftment of CPCs. The lower panel shows higher magnification images of the corresponding field of view in the upper image.

D) Immunohistochemical staining with caspase 3 and collagen II was performed on the blood flow-inhibited transplant model (upper panel) and a normal transplant model (lower panel) (scale bar: 200 μm).

Figure 9:
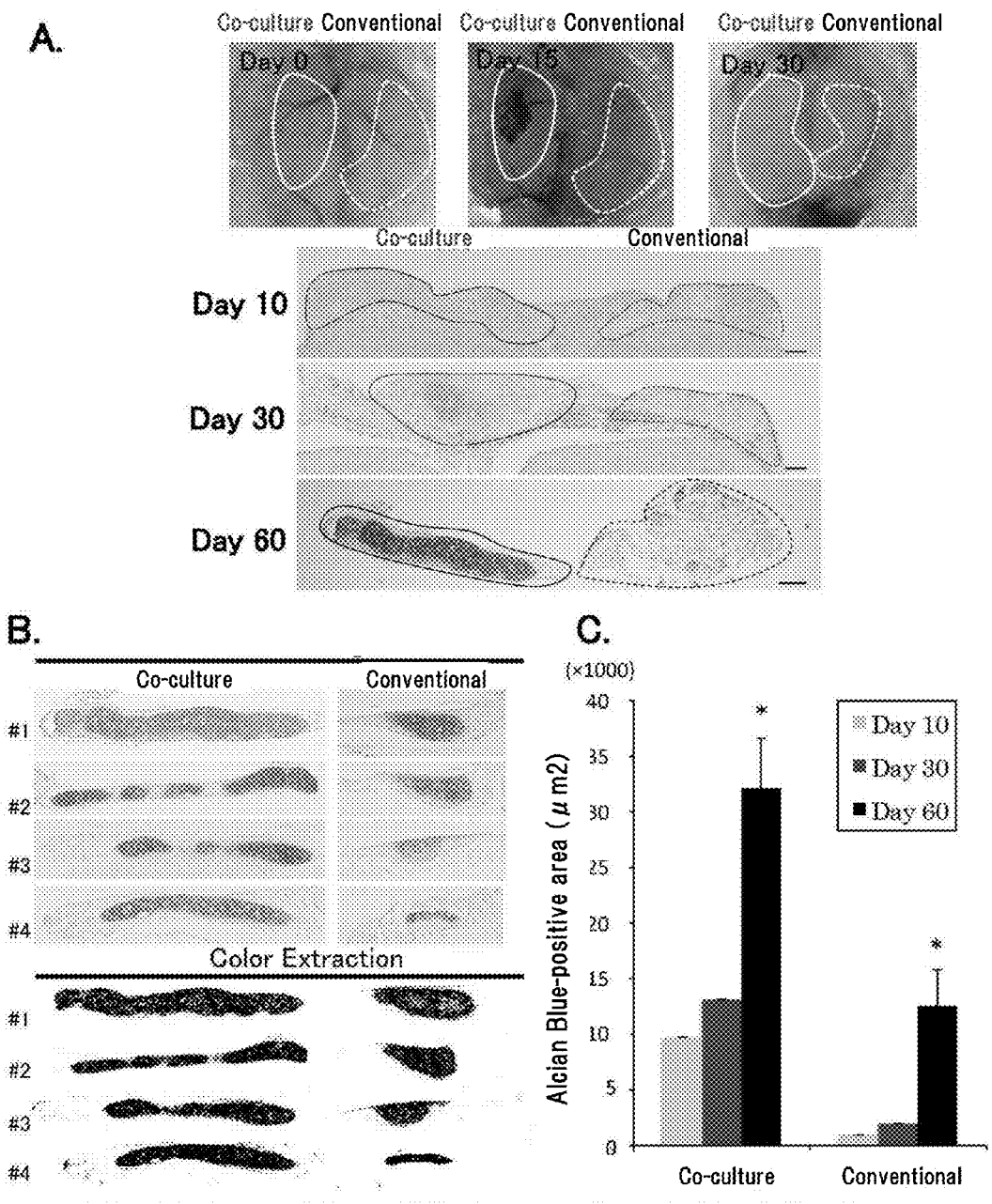

FIG. 9 Highly Efficient Generation of Elastic Cartilage from Three-Dimensional Tissues Constructed by Co-culture with Vascular Endothelial Cells A) CPCs co-cultured with HUVEC were transplanted into the left cerebral hemisphere of a cranial window mouse, and a pellet culture of CPCs was transplanted into the right cerebral hemisphere of the same cranial window mouse. At day 15 of transplantation, the CPCs co-cultured with HUVEC had begun producing proteoglycans earlier than the pellet transplant. At days 30 and 60 of transplantation, the CPCs co-cultured with HUVEC differentiated into mature chondrocytes (scale bar: 200 μm).

B) Comparison of Alcian Blue positive area in sections taken from the widest point of the samples between the CPCs co-cultured with HUVEC and pellet transplants, and color extraction images of those sites stained in blue. Color extraction was performed with Image J.

C) Alcian Blue positive area was quantified. Data are shown as the mean±s.d. obtained from at least independent specimens (N=4; *: P<0.05).

Figure 10:
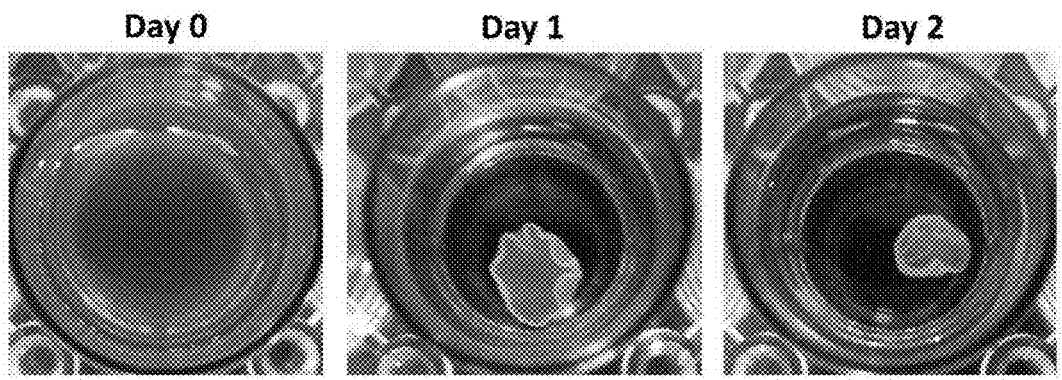

FIG. 10 Perichondrocytes ($3 \times 10^6$) and vascular endothelial cells ($1 \times 10^6$) were cultured on a gel with a hardness of 0.5 kPa (hydrogel for cell cultivation; sample plate for evaluation (VERITAS)). The states of three-dimensional tissue formation at days 0, 1 and 2 of culture are shown.

Figure 11:
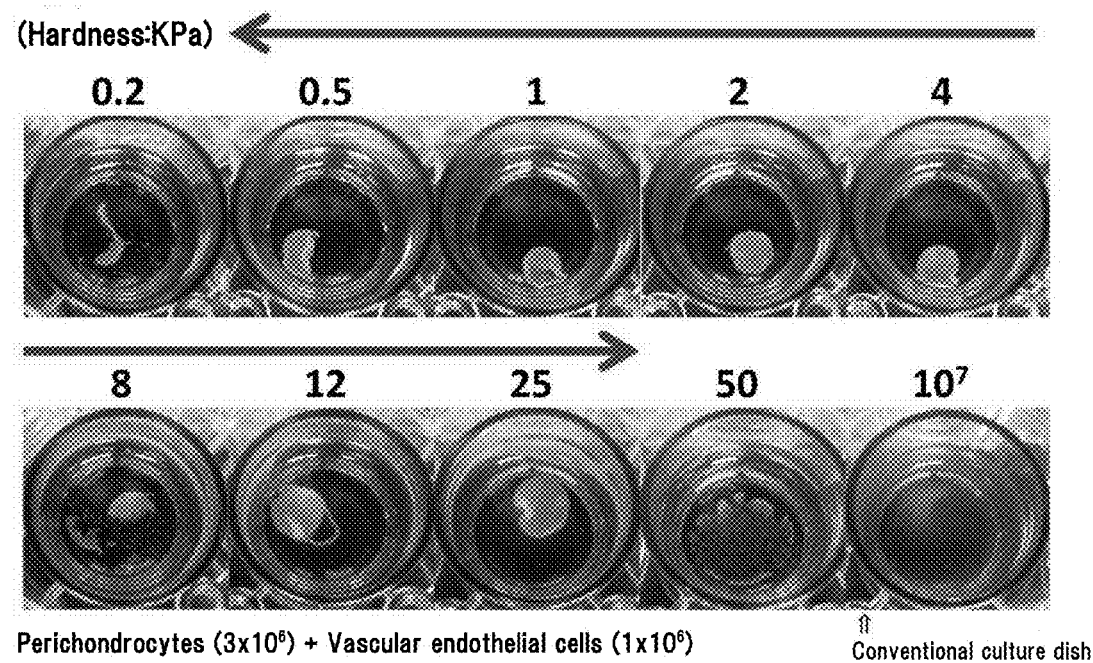

FIG. 11 Perichondrocytes ($3 \times 10^6$) and vascular endothelial cells ($1 \times 10^6$) were cultured on a gel with a hardness of 0.2-50 kPa (hydrogel for cell cultivation; sample plate for evaluation (VERITAS)). The states of three-dimensional tissue formation at day 2 of culture are shown. The rightmost image in the lower panel shows the state when culture was performed in the same manner on a conventional culture dish (three-dimensional tissues were not formed).

Figure 12:
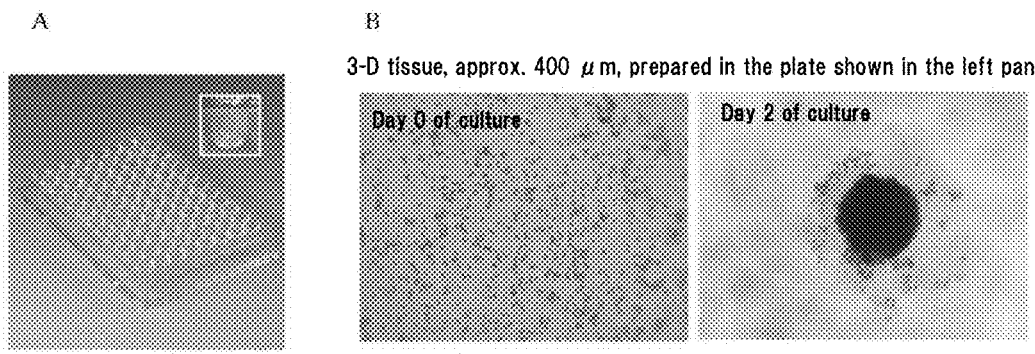

FIG. 12 Perichondrocytes ($3\times10^4$) and vascular endothelial cells ($1\times10^4$) were cultured on a culture substrate having a U-shaped bottom. The states of three-dimensional tissue formation at days 0 and 2 of culture are shown. A) Appearance of a 96-well cell culture substrate having a U-shaped bottom (Sumitomo Bakelite). The upper-right panel shows an enlarged image of a single well. B) The seeded perichondrocytes began to aggregate autonomously and formed spheres of three-dimensional tissue with an approximate size of 400 μm the day after the seeding.

Figure 13:
Figure 13:

FIG. 13 One hundred (100) three-dimensional tissues 4 mm in size formed by co-culturing perichondrocytes ($3\times10^6$) and vascular endothelial cells ($1\times10^6$) were subcutaneously transplanted. The states of transplantation are shown. A) The state in which a large amount of three-dimensional tissues were located subcutaneously. B) Approximately 30 three-dimensional tissues are being recovered with a spatula.

Figure 14:
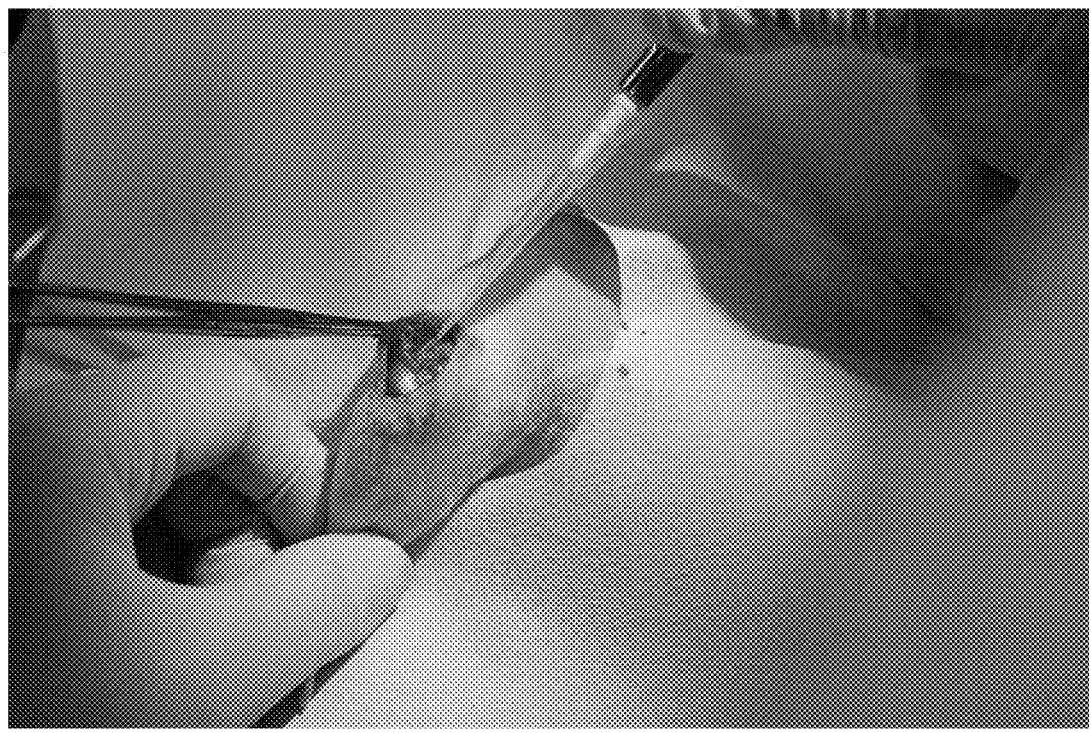
Figure 14:

FIG. 14 Six hundred (600) three-dimensional tissues 400 μm in size formed from perichondrocytes ($3\times10^4$) and vascular endothelial cells ($1\times10^4$) were transplanted into a deficient site of an articular cartilage. The states of transplantation are shown. A) Three-dimensional tissues with an approximate size of 400 μm as recovered in large quantity are being transplanted into a deficient site of an articular cartilage with a pipette. B) The appearance of the deficient site of the articular cartilage immediately after transplantation of the three-dimensional tissue.

Figure 15:
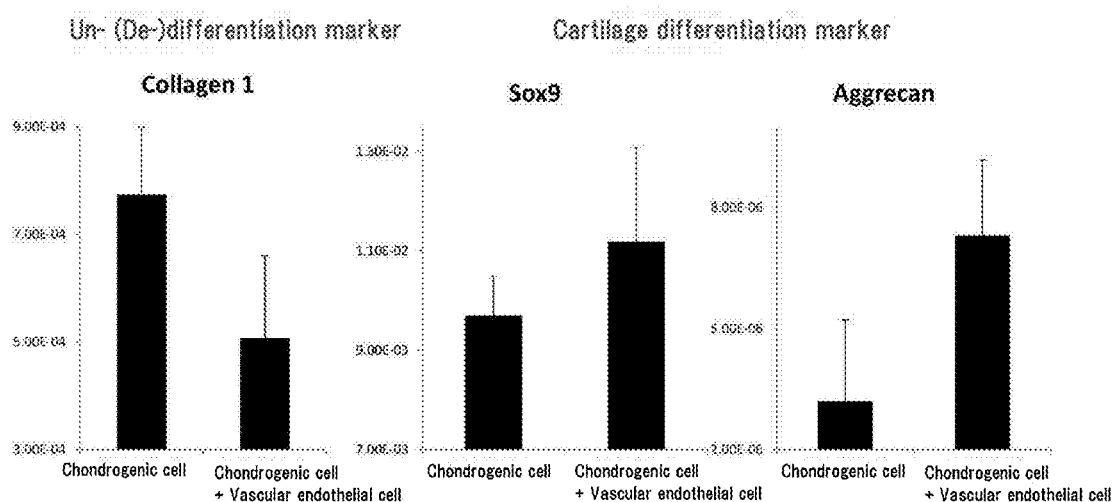

FIG. 15 Gene expression analyses are shown for chondrogenic cells cultured alone and chondrogenic cells co-cultured with vascular endothelial cells. Left panel: Expression of undifferentiation (dedifferentiation) marker. Right panel: Expression of cartilage differentiation markers.

Figure 16:
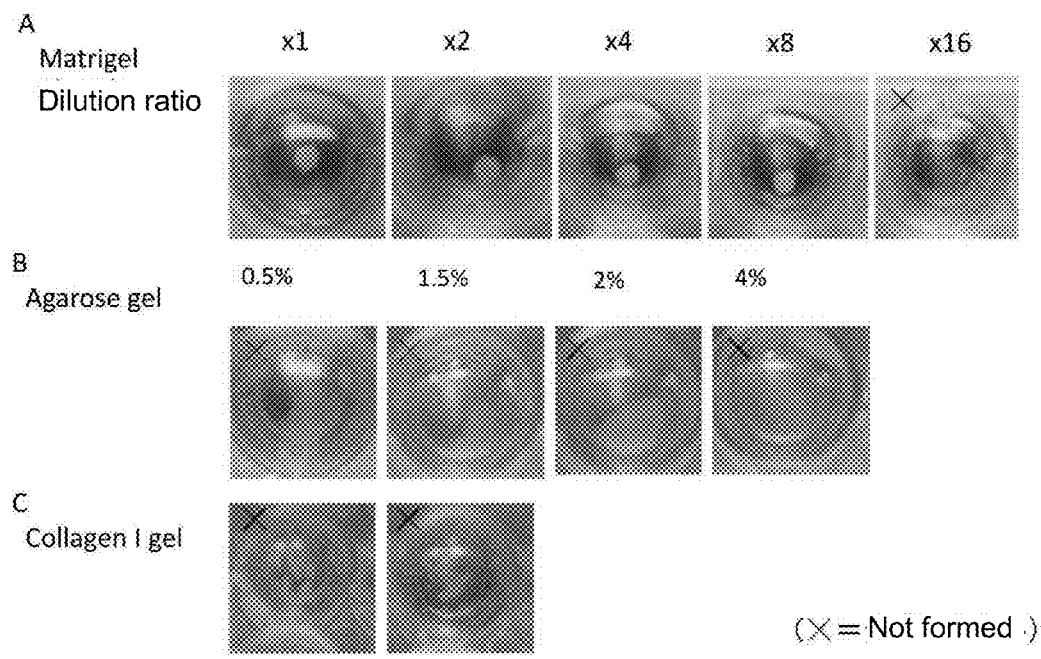

FIG. 16 Study on the requirements of supports suitable for use in the preparation of vascularized cartilage. A) Study on Matrigel™ dilution rates revealed that up to 8-fold dilution is able to yield vascularized cartilage. B) When agarose gel was used, vascularized cartilage was not formed under any conditions. C) When collagen I gel was used, vascularized cartilage was not formed either.

Figure 17:
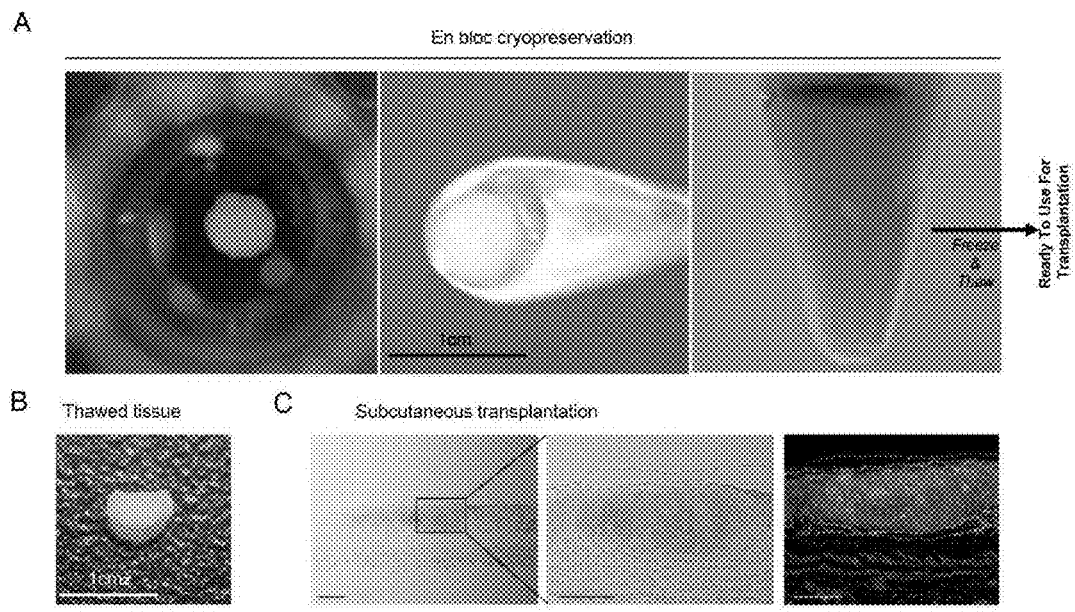

FIG. 17 Generation of Human Mature Cartilage by Transplantation of Cryopreserved Vascularized Cartilage. A) Cryopreservation process for vascularized cartilage. Left panel: Tissue formed in a culture dish. Middle panel: Tissues recovered with a spatula. Right panel: The recovered tissues were dipped in cryopreservation solvent (TC protector) immediately before freezing. B) Gross observation of human vascularized cartilage thawed one month after freezing. C) Histological analysis of subcutaneously transplanted sample of thawed human vascularized cartilage. The vascularized cartilage was subcutaneously transplanted into the back of immunodeficient mice and removed two months post transplantation. As it turned out, cartilage tissues had been reconstructed in which Alcian Blue staining and collagen II production were recognizable.

Figure 18:
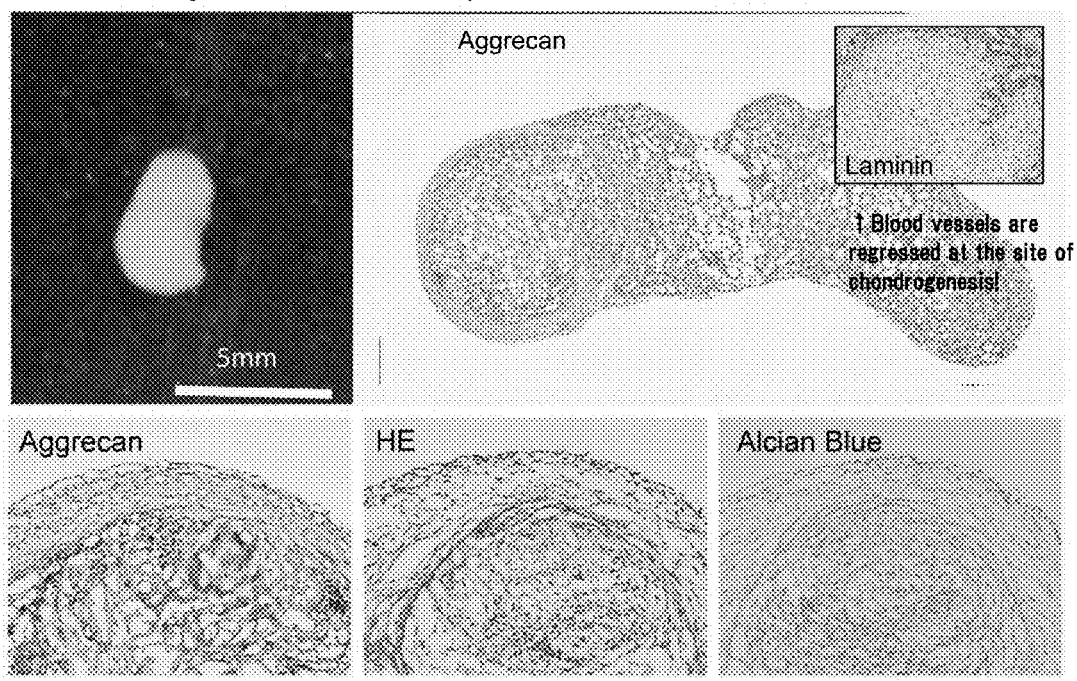

FIG. 18 Generation of Mature Cartilage Derived from Vascularized Cartilage after Long-Term Culture. Histological analysis of long-term cultured vascularized cartilage. By culturing the prepared vascularized cartilage for a period as long as 60 days, formation of blood vessel-containing perichondral tissue and blood vessel-free cartilage tissue was observed. Upper left panel: macroscopic image of the formed tissue. Upper right panel: by immunostaining showed, the central part was shown to express the cartilage marker aggrecan while it was surrounded by laminin. Lower left panel: enlarged image of immunostaining Lower middle panel: HE staining. Lower right panel: Alcian Blue staining. The induced three-dimensional tissue had such a high mechanical strength that it was not destroyed even when manually compressed with tweezers.

Figure 19:
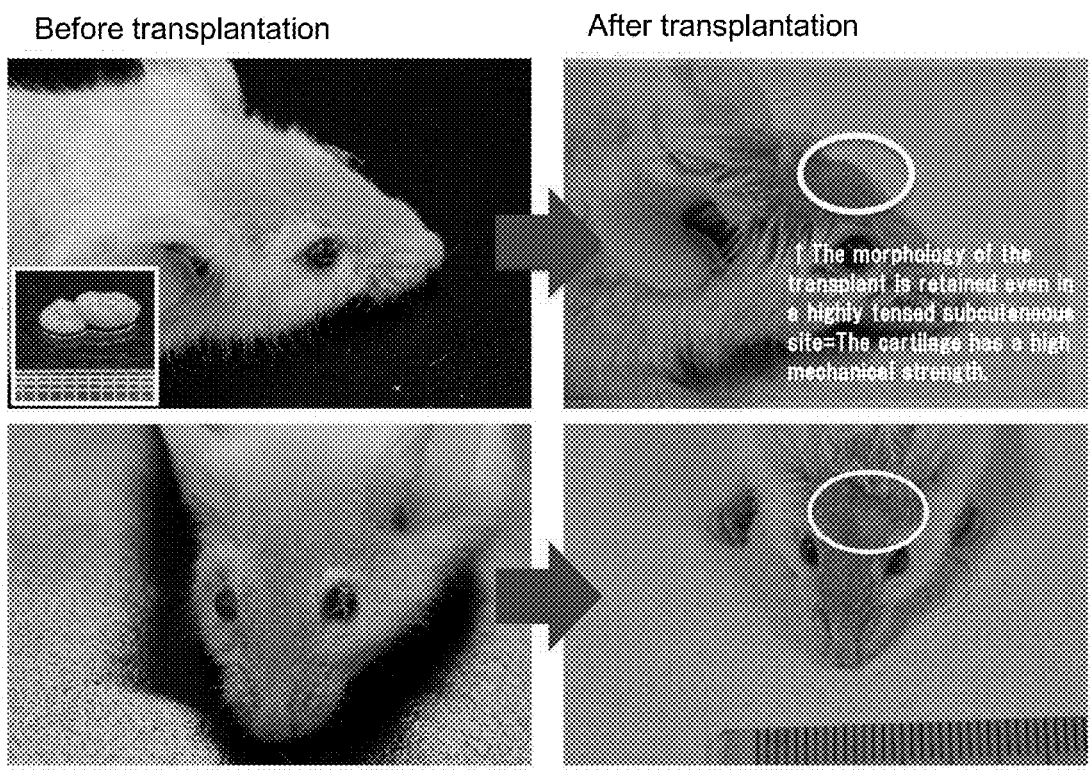

FIG. 19 Transplantation of Mature Cartilage Derived from Vascularized Cartilage after Long-Term Culture. Long-term cultured vascularized cartilage (shown in a small window at the left lower corner of upper left panel) was transplanted into a facial site and found to have a sufficient mechanical strength to withstand subcutaneous tension. Upper and lower photographs were taken to confirm the raised portion as viewed from different angles.

BEST MODE FOR CARRYING OUT THE INVENTION

Hereinbelow, the present invention will be described in detail.

The present invention provides a method for preparing chondrocytes, comprising co-culturing chondrogenic cells with vascular cells.

The term "chondrogenic cells" used in the present invention refers to cells capable of forming cartilage. For example, cells that express markers such as BRACHYURY, KDR, CXCR4, PDGFRA, PDGFRB, CD44, SOX5, SOX6, SOX9, RUNX2, CDH1, Aggrecan, collagen II, versican, elsatin, CSP, etc. are preferable.

Chondrogenic cells may be obtained from various sources. Generally, chondrogenic cells are isolated from ear cartilage or ear perichondrium, but their sources are not limited to these two. Further, chondrogenic cells may be classified into chondrocytes, immature chondrocytes, cartilage progenitor cells, cartilage stem cells, or the like. Chondrocytes may be obtained from any of the following cartilages: hyaline cartilage, elastic cartilage or fibrocartilage. Specifically, chondrocytes are obtained from rib cartilage, nasal cartilage, ear cartilage, tracheal cartilage, pharyngeal cartilage, thyroid cartilage, arytenoid cartilage, cricoid cartilage, tendon, ligament, interarticular cartilage, intervertebral disc and the like. Generally, it is believed that cultured chondrocytes are dedifferentiated. Such dedifferentiated chondrocytes may also be used. Immature chondrocytes, cartilage progenitor cells or cartilage stem cells are obtained from tissues such as cartilage, perichondrium, bone marrow, placenta, umbilical cord, skin, muscle, fat, periosteum and the like. As chondrogenic cells, those derived from human may be used mainly. Chondrogenic cells derived from non-human animals (e.g., animals used for such purposes as experimental animals, pet animals, working animals, race horse and fighting dog; more specifically, mouse, rat, rabbit, pig, dog, monkey, cattle, horse, sheep, chicken, shark, devilfish, ratfish, salmon, shrimp, crab or the like) may also be used.

Vascular cells may be isolated from vascular tissue. However, vascular cells are not limited to those isolated from vascular tissue. Vascular cells differentiated from totipotent or pluripotent cells (e.g., iPS cells or ES cells) may also be used. As vascular cells, vascular endothelial cells are preferable. The term "vascular endothelial cells" used in the present invention refers to cells constituting vascular endothelium or cells capable of differentiating into such cells (e.g., vascular endothelial progenitor cells, vascular endothelial stem cells and the like). Whether a specific cell is vascular endothelial cell or not may be determined by checking for the expression of marker proteins such as TIE2, VEGFR-1, VEGFR-2, VEGFR-3 or CD31 (if any one or a plurality of the above-listed marker proteins are expressed, the cell may be judged as vascular endothelial cell). As markers for vascular endothelial progenitor cells, c-kit, Sca-1 and so on have been reported. If these markers are expressed, the cells of interest may be confirmed as vascular endothelial progenitor cells (S Fang, et al., PLOS Biology 2012; 10(10):e1001407). Among the relevant terms used by those skilled in the art, endothelial cells, umbilical vein endothelial cells, endothelial progenitor cells, endothelial precursor cells, vasculogenic progenitors, hemangioblast (H J. Joo, et al., Blood 25; 118(8):2094-104 (2011)) and the like are also encompassed in the vascular endothelial cells used in the present invention. As vascular cells, those derived from human may be used mainly. Vascular cells derived from non-human animals (e.g., animals used for such purposes as experimental animals, pet animals, working animals, race horse and fighting dog; more specifically, mouse, rat, rabbit, pig, dog, monkey, cattle, horse, sheep, chicken, shark, devilfish, ratfish, salmon, shrimp, crab or the like) may also be used. Vascular cells may be obtained from umbilical cord blood, umbilical cord vessel, neonatal tissue, liver, aorta, brain, bone marrow, fat tissue and the like.

Chondrogenic cells and vascular cells may be any of the following cells: cells taken from organisms, primary or sub-cultures of cells taken from organisms, or cell lines established therefrom, cells differentiated from totipotent or pluripotent cells (such as immature cells, progenitor cells, stem cells, iPS cells, ES cells or the like). Further, chondrogenic cells and vascular cells may be derived either from the same individual or from different individuals. When application to regenerative therapy is intended, chondrogenic cells and vascular cells (especially, vascular cells) are preferably HLA-matched to avoid immune rejection.

The mixing ratio of the two types of cells to be co-cultured is not particularly limited as long as it is within the range that enables formation of cartilage. A preferable ratio in cell count is 1 (chondrogenic cells) vs 0.4-1 (vascular cells).

By co-culturing chondrogenic cells with vascular cells, the interactions between chondrogenic cells and vascular cells cause the chondrogenic cells to change into the state of pre-chondrocytes (immature chondrocytes) as predestined for cartilage. At the same time, cell proliferation is activated.

The concept of the "chondrocytes" prepared by the method of the present invention encompasses not only completely differentiated chondrocytes but also pre-chondrocytes (immature chondrocytes), cartilage progenitor cells, cartilage stem cells, mixtures thereof, and the like. Differentiation into cartilage may be confirmed by Alcian Blue staining, decreased expression of markers indicating undifferentiated (dedifferentiated) state (e.g., collagen I or CD44), enhanced expression of cartilage differentiation markers (e.g., Sox9, RUNX2, aggrecan, collagen II, versican, elastin or CSPG), etc.

By co-culturing chondrogenic cells with vascular cells, chondrogenic cells amplify. (See Example 1 provided later and FIG. 6.) Amplification of cells means that cells proliferate by self-replication.

Further, by co-culturing chondrogenic cells with vascular cells, three-dimensional tissues may be formed. The three-dimensional tissues may be formed by co-culturing chondrogenic cells with vascular cells on a support. The support may be a substrate with a hardness of 0.5-25 kPa. Examples of such a substrate include, but are not limited to, gels (e.g., Matrigel™ either in stock solution or diluted up to 4-fold, agarose gel, acrylamide gel, hydrogel, collagen gel or urethane gel). It is possible to form three-dimensional tissues of a large size (approximately 2 to 3 mm or larger) on a substrate with a hardness of 0.5-25 kPa. Such large-sized three-dimensional tissues are suitable for subcutaneous mass transplantation. (See Example 4 provided later and FIG. 13.)

Alternatively, it is also possible to form three-dimensional tissues by co-culturing chondrogenic cells and vascular cells not on a support such as gel but on a plate having a shape in which cells gather in the bottom (e.g., a U-shaped or V-shaped bottom). Small-sized (i.e., approximately several hundred μm or smaller) three-dimensional tissues may be formed on such a plate. Such small-sized three-dimensional tissues are suitable for transplantation into deficient sites in articular cartilage. (See Example 5 provided later and FIG. 14.)

Formation of three-dimensional tissues is observed about one day from the beginning of co-culture of chondrogenic cells and vascular cells. Upon further culture (about two days from the beginning of the co-culture), formation of vasculatures is recognized in the three-dimensional tissues. In the subsequent period (about ten days from the beginning of the co-culture), the vasculatures were confirmed to disappear.

The medium for the co-culture may be any medium capable of maintaining chondrogenic cells and vascular cells. The medium may contain at least one component selected from the group consisting of fibroblast growth factor 2 (bFGF (FGF2)), fibroblast growth factor 5 (FGF5), bone morphogenetic protein 2 (BMP2), bone morphogenetic protein 4 (BMP4), bone morphogenetic protein 6 (BMP6), connective tissue growth factor (CTGF), transforming growth factor β1 (TGF-β1), transforming growth factor β2 (TGF-β2), transforming growth factor β3 (TGF-β3), insulin-like growth factor 1 (IGF-1), hepatocyte growth factor (HGF), fibroblast growth factor 4 (FGF4), bone morphogenetic protein 3 (BMP3), aggrecan, hyaluronic acid, endothelial cell growth factor (ECGF), endothelial cell growth supplement (ECGS), endothelial cell-derived growth factor (ECDGF), epidermal growth factor (EGF), acidic fibroblast growth factor (acidic FGF), macrophage-derived growth factor (MDGF), platelet-derived growth factor (PDGF), tumor angiogenesis factor (TAF), vascular endothelial growth factor (VEGF), bovine brain extract (BBE), bovine pituitary extract (BPE), glucocorticoid, cholesterol, and vitamins. These growth factors or hormones may be added to the medium either alone or in suitable mixtures. Examples of glucocorticoid include, but are not limited to, hydrocortisone, cortisone, corticosterone, dexamethasone, triamcinolone and prednisolone. Examples of vitamins include vitamin C and the like. bFGF (FGF2), FGF5, FGF5, BMP2, BMP4, BMP6, CTGF, TGF-β1, TGF-β2, TGF-β3, IGF-1, HGF, EGF, FGF4, BMP3, aggrecan and hyaluronic acid are capable of supporting differentiation into cartilage. Endothelial cell growth factor (ECGF), endothelial cell growth supplement (ECGS), endothelial cell-derived growth factor (ECDGF), epidermal growth factor (EGF), acidic fibroblast growth factor (acidic FGF), basic fibroblast growth factor (bFGF), insulin-like growth factor-1 (IGF-1), macrophage-derived growth factor (MDGF), platelet-derived growth factor (PDGF), tumor angiogenesis factor (TAF), vascular endothelial growth factor (VEGF), bovine brain extract liquid (BBE), bovine pituitary extract (BPE), glucocorticoids (hydrocortisone, cortisone, coach corticosterone, dexamethasone, triamcinolone, prednisolone, etc.), cholesterol, vitamins and so forth are capable of supporting the survival of vascular cells. Incidentally, presence of protein preparations such as those listed above is not essential for the formation of three-dimensional tissues; any medium may be used as long as it is capable of maintaining vascular cells.

The differentiation of three-dimensional tissues may be at any stage, such as pre-chondrocyte (immature chondrocyte) or mature chondrocyte.

The shape of three-dimensional tissues is usually spherical. However, a complex shape such as ear may be formed by selecting an appropriate substrate. Thus, the shape of three-dimensional tissues is not particularly limited.

The three-dimensional tissue formed by the method of the present invention may have such a high mechanical strength that it will not be destroyed even if it is manually compressed with tweezers.

The temperature for culturing is not particularly limited and it is preferably 30-40° C., more preferably 37° C.

The period of culture is not particularly limited and it is preferably 1-20 days, more preferably 2-3 days.

The chondrocytes prepared by the above-described method—which may be any of completely differentiated chondrocytes, pre-chondrocytes (immature chondrocytes), cartilage progenitor cells, cartilage stem cells or a mixture thereof and may or may not form three-dimensional tissues—may be cryopreserved. Further, the frozen chondrocytes may be thawed befire use. Therefore, the method of the present invention for preparing chondrocytes may comprise a step of freezing chondrocytes. Further, the method of the invention may comprise a step of thawing the frozen chondrocytes.

The chondrocytes prepared by the method of the present invention may be used in cartilage regenerative therapy. Therefore, the present invention provides a composition for use in cartilage regenerative therapy, comprising the chondrocytes obtained by co-culturing chondrogenic cells with vascular cells.

Those chondrocytes which have formed three-dimensional tissues as a result of co-culture of chondrogenic cells and vascular cells are preferable because they are easy to transplant. Even when the chondrocytes have not formed three-dimensional tissues, it is believed that regeneration of cartilage is possible if those cells can be kept in place without dispersing after transplantation. For example, it is believed that the chondrocytes can be transplanted even if they are in the state of a pellet (a state in which all the cells have been precipitated by centrifugation).

The composition of the present invention may be used for transplantation into an organism to induce the formation of cartilage tissues. Therefore, the present invention also provides a method for cartilage regeneration, comprising transplanting the chondrocytes prepared by the above-described method into an organism to induce the formation of cartilage tissues.

Examples of organisms include human and non-human animals (e.g., animals used for such purposes as experimental animals, pet animals, working animals, race horse and fighting dog; more specifically, mouse, rat, rabbit, pig, dog, monkey, cattle, horse, sheep, chicken, shark, devilfish, ratfish, salmon, shrimp, crab or the like).

When the composition of the present invention has been transplanted into an organism, a vascular network can be constructed. (See Example 1 provided later, as well as FIGS. 2C, 3 and 4.) Vascular perfusion may occur in the vascular network. As a result of vascular perfusion taking place in the vascular network, chondrogenic cells can engraft efficiently. The vascular network once constructed disappears, potentially resulting in the formation of an vascular cartilage tissue. (See Example 1 provided later, as well as FIGS. 2C, 3 and 4.) Once induction of differentiation into chondrocytes has begun, vasculatures are gradually eliminated while, at the same time, terminal differentiation of chondrogenic cells occurs. (See Example 1 provided later, as well as FIGS. 2C, 3 and 4.)

For the purpose of transplantation into organisms, three-dimensional tissues about three days after the beginning of co-culture seem to be suitable. To form a large-sized cartilage, three-dimensional tissues with an approximate size of 3 mm may be transplanted subcutaneously in large quantity (several to several tens of tissues; Example 4 provided later and FIG. 13). For transplantation into a deficient site in joint, several hundreds of three-dimensional tissues approximately 200-400 µm in size may be transplanted (Example 5 provided later and FIG. 14). Speaking of vasculatures, good results are often produced if they are recognizable but their presence is not essential. It seems important that three-dimensional tissue formation be physically (macroscopically) good enough to present a certain degree of hardness.

The present invention provides a technique to prepare a therapeutic three-dimensional cartilage device. This cartilage device is intended to realize cartilage regenerative therapy for those patients with deformations in face and those patients with joint diseases caused by traumas resulting from aging or sport activities. Cartilage regenerative therapy will become feasible which has by far superior clinical therapeutic effects over the current surgical treatment or the conventional technology of regenerative therapy.

The chondrocytes prepared by the method of the invention may also be used in screening for drugs effective as pharmaceuticals. According to the present invention, it has become possible to reconstruct disease model three-dimensional cartilage tissues from chondrogenic cells harvested from patients with cartilage degenerative diseases. The reconstructed disease model three-dimensional cartilage tissue is expected to provide a screening system beneficial for developing new drugs. Therefore, the present invention provides a method of screening for drugs effective as pharmaceuticals, comprising using chondrocytes prepared by co-culturing chondrogenic cells and vascular cells, a cartilage tissue formed from the chondrocytes and/or cells derived from the cartilage tissue.

For example, screening for compounds which promote chondrogenesis using the formed three-dimensional tissues as target will lead to the development of pharmaceuticals effective when cartilage is damaged. In this screening process, effective drugs can be selected by, for example, adding candidate substances to a culture system for three-dimensional tissues and checking for the presence or absence of promoted chondrogenesis.

Other example is as follows; screening for compounds which inhibit inflammatory responses will lead to the development of pharmaceuticals effective for treating such diseases as rheumatic disease and degenerative arthritis. In this screening process, effective drugs can be selected by, for example, adding drugs to a culture system for three-dimensional tissues prepared using synoviocytes or chondrocytes harvested from patients with autoinflammatory joint diseases and then checking to see whether production of collagenase and protease (tissue-lysing enzymes) which are involved in autoinflammatory joint diseases is inhibited or not.

Test substances supplied to the screening method of the present invention may be any known compounds and/or novel compounds. Further, test substances may be either one or both of high molecular weight compounds (e.g., nucleic acids, saccharides, lipids, proteins, peptides, etc.) and/or low molecular weight compounds. These substances may be derived from nature (e.g., natural components derived from microorganisms, animals, plants, marine organisms or the like) or may be synthesized (e.g., existing compound libraries, compound libraries prepared by combinatorial chemistry technology, peptide libraries, virtual libraries or the like).

Further, the chondrocytes prepared by the method of the present invention may be used for preparing substrates that chondrocytes produce. Chondroitin sulfate extracted from cartilage tissues derived from animals such as shark is widely used as a health-promoting food. The cartilage tissues artificially reconstructed by the method of the present invention will be a source of supply of cartilage tissues which are extremely beneficial for efficient production of chondroitin sulfate in food related industries. Therefore, the present invention provides a method for preparing a substrate produced by chondrocytes, comprising using chondrocytes prepared by co-culturing chondrogenic cells and vascular cells, a cartilage tissue formed from the chondrocytes and/or cells derived from the cartilage tissue. In addition to chondroitin sulfate, examples of matrixes produced by chondrocytes include, but are not limited to, hyaluronic acid, proteoglycan, collagen and elastin. Known methods for extracting matrixes from cell or tissue cultures may be used to prepare matrixes produced by chondrocytes through the use of chondrocytes prepared by co-culturing chondrogenic cells and vascular cells, a cartilage tissue formed from the chondrocytes and/or cells derived from the cartilage tissue.

EXAMPLES

Hereinbelow, the present invention will be described in more detail with reference to the following Examples.

Example 1 Generation of Elastic Cartilage Using Human Cartilage Progenitor Cells 1. Abstract Adult cartilage tissue is a simple tissue lacking blood vessels and neurons. Compared to solid organs with complex higher structures, early realization of cartilage regenerative therapy is expected. A number of studies have been reported in which various tissue-derived mesenchymal progenitor cells are used to make an attempt at inducing differentiation into mature chondrocytes. However, in conventional methods of inducing differentiation using growth factors, low efficiency of inducing terminal differentiation into chondrocytes remains a serious problem to be solved.

In the present research, an attempt was made to elucidate physiological differentiation processes of cartilage with the aim of developing a highly efficient method of generating elastic cartilage. Ear cartilage at an early development stage containing cartilage progenitor cells (CPCs) was introduced into a unique, live observation system, followed by tracking-type fixed point observation in vivo. As it turned out, transient blood perfusion was found to occur causing invasion of vascular endothelial cells. Clearly, this temporarily enhanced the proliferative activity of CPCs and the subsequent regression of blood vessels was accompanied by induction of terminal differentiation. Then, the present inventors attempted to construct a novel culture system which would recapitulate the transient vascular invasion in the above-described developmental process, using the human CPCs recently identified by the present inventors. Surprisingly, it has become clear that CPCs will construct three-dimensional tissues in vitro in a self-driven manner by co-culture with vascular endothelial cells. Further, it has been shown that when the thus constructed three-dimensional tissues are used in transplantation, they reconstruct elastic cartilage in a highly efficient manner as compared with the conventional pellet transplantation method.

According to this technology, there is no need to use growth factors or scaffold materials. Therefore, this technology is expected to become an elastic cartilage reconstruction technology that is extremely beneficial in view of safety and cost. It is believed that a new therapy for treating tissue deformations caused by congenital defects or traumas in craniofacial area can be provided in future by co-culturing a patient's HLA-matched vascular endothelial cells with CPCs harvested in a minimally invasive manner and cultured, inducing three-dimensional organization, and transplanting the resultant three-dimensional tissue into the patient.

2. Introduction

More than one million patients worldwide are affected by craniofacial deformations caused by congenital defects or traumas, and development of a new treatment method for these patients is eagerly awaited[1]. Current surgical treatments for facial deformations or congenital defects generally rely on the use of autologous cartilage tissue grafts[2]. One example of cartilage tissue widely used in tissue transplantation is rib cartilage. However, surgeries for taking a rib cartilage graft raise problems of post-surgical pain and scar in the breast; moreover, in some cases, such surgeries cause precordial deformations. Since surgeries to treat congenital defects are often performed in childhood, invasion into patients is relatively high and the burden on patients is immeasurable. Further, yearly tissue deformation and absorption resulting from cartilage tissue transplantation and monthly tissue absorption resulting from bone tissue transplantation are extremely serious problems, failing to produce clinically satisfactory long-term results[3-7]. Although it is possible to transplant biomedical materials such as synthetic high molecular weight compounds[8-13], they are known to cause infection, inflammation or dermal perforation because they are foreign substances to human bodies; these problems still remain to be solved[12,13]. As a novel treatment method which can overcome the above-described problems, a method of clinical reconstruction of human elastic cartilage using tissue regeneration engineering is eagerly desired.

As cell sources applicable to reconstruction of human elastic cartilage, several potentials have been suggested[14-16]. Although human ear chondrocyte is superior in such aspects as cartilage differentiation potency, this cell not only involves the problem of invasion into the site of cell collection but also has a problem in that long-term tissue maintenance is difficult to achieve due to the cell's short life because there are no stem cells with self-replication competence. Bone marrow-derived human mesenchymal cell is one of those cells which may potentially resolve the above problems[17,18]. However, this cell has various problems such as bone marrow aspiration being highly invasive, potency of differentiation into mature chondrocytes being extremely low, and vascular invasion or calcinosis being likely to occur and, therefore, the potential of this cell for practical application is low[19-21]. Although there are other candidates such as fat tissue-derived human mesenchymal stem cells, such cells are low in the potency of differentiation into mature chondrocytes and their capacity to produce extracellular substrate in elastic cartilage has not been confirmed at all.

Thus, excellent cell sources applicable to reconstruction of human elastic cartilage have not been found yet[22-24].

For realization of regenerative therapy with human elastic cartilage, it is necessary to identify human cartilage progenitor cells which may be collected by a low invasive operation and have high proliferative activity, high potency of differentiation into mature chondrocytes and self-replication competence, and to develop various cell manipulating techniques related to methods of isolation/culture of the identified cells and differentiation induction method for the identified cells.

In a prior study, the present inventors have confirmed by BrdU labeling retaining assay that label retaining cells (LRCs) are present only in the perichondrium of mouse ear for one year after BrdU administration[25]. This result suggested that cartilage progenitor cells (CPCs) are present in perichondrium. Then, the present inventors have revealed the presence of a cell population with high proliferative capacity and pluripotency (which are two characteristic features of progenitor cells) in human perichondrium, and developed a technique for isolating/culturing progenitor cells[26].

On the other hand, molecular biological analyses were performed with the aim of searching for factors which induce differentiation into chondrocytes, and it has become clear that a variety of growth factors regulating proliferation/differentiation intervene in the progress of cartilage differentiation. As one example, FGFs (fibroblast growth factors) may be given. FGFs were found in 1974 by Gospodarowicz et al. as growth factors promoting proliferation of fibroblasts in bovine brain extract[27]; purification of FGFs from calf cartilage was successfully made in 1977[28]. It has become clear that mutation in FGFR gene results in the onset of hereditary osteogenic diseases such as chondrodysplasia or hypochondroplasia[29,30] causing craniosynostosis or limb shortening. The role of FGF signals in the formation of bone/cartilage has been attracting researchers' attention. Further, transgenic mice expressing a dominant negative receptor deficient of the kinase region of TGF-β receptor presented knee osteoarthritis-like conditions[31]. Molecular biological analyses have revealed that Smad2/3-mediated signal by TGF-β promotes the transcription activity of Sox9 and regulates complex formation between Sox9 and CPB/p300 in the enhancer region of Col2a1 gene, thereby promoting early differentiation of cartilage[32]. From these results, it is believed that addition of growth factors such as TGFs or FGFs is necessary to induce differentiation of CPCs or mesenchymal stem cells into cartilage[33,34]. Actually, inducing differentiation of CPCs into cartilage by adding two growth factors, insulin-like growth factor-1 and basic FGF, is a standard method. However, a problem with this method is that efficiency of cartilage reconstruction is low for several reasons such as low engraftment ratios. Likewise, many studies have been made to induce differentiation in mesenchymal stem cells into cartilage[35-38], but each of those methods has the problem of low efficiency in cartilage reconstruction.

During early stages of development, CPCs differentiating from undifferentiated mesenchymal cells emerge and differentiate/mature into chondrocytes through mesenchymal condensation. As a result, cartilage tissues are formed. However, physiological differentiation processes of CPCs have much to be elucidated. Under the circumstances, the present inventors have attempted to develop a highly efficient method of generating elastic cartilage by elucidating the totally unknown physiological differentiation processes and recapitulating the interactions between those processes.

3. Materials and Methods 3-1. Preparation of Cranial Windows

Six-week-old female NOD/SCID mice were purchased from Sankyo Lab. Co. and bred and maintained at Animal Experiment Center, Joint Research Support Section, Advanced Medical Research Center, Yokohama City University. Animal experiments using these mice were performed in accordance with the Yokohama City University Fukuura Campus Animal Experiment Guidelines.

Preparation of cranial windows was performed mainly according to the method of Yuan et al.[39] For anesthetization, 90 mg/kg of ketalar (Sankyo Yell Yakuhin Co.) and 9 mg/kg xylazine (Sigma Chemical Co.) were mixed with sterilized PBS to give a dose of 200 μl per mouse and intramuscularly injected into the thigh (ketalar/xylazine mixed anesthesia). Ketalar was used according to the Narcotics Administration Law. The heads of NOD/SCID mice were sterilized with 70% ethanol. The skin on the head was incised. The periosteum on the surface of the skull was removed with cotton swab. Subsequently, the skull was thinly cut with a dental microdrill (Fine Science Tools) in a circular manner, and the resultant circular portion was removed carefully. Then, the dura was scraped off with tweezers. When bleeding occurred, hemostasis was performed with spongel (Astellas Co.). After confirmation of the absence of bleeding, the surface of the brain was filled with physiological saline (Otsuka Pharmaceutical Co.). Then, a custom-made circular slide glass 7 mm in diameter (Matsunami) was mounted thereon and sealed tightly with an adhesive prepared by mixing coatley plastic powder (Yoshida) with Aron Alpha (Toagosei Co.) until the mixture become cementitious.

One week after the preparation of cranial windows, those mice which did not have bleeding or inflammation at the site of surgery were selected and used in the subsequent experiments.

3-2. Confocal Microscopy

Ketalar/xylazine mixed anesthesia was administered intraperitoneally to the thus prepared cranial window mice, which were then laid on their back so that the glass in the head became horizontal. The mice were fixed on cover glasses with cellophane tape, followed by observation of immature cartilage tissues and cells of GFP-mouse (C57BL/6-Tg (CAG-EGFP)) (Japan SLC)[40,41]. A confocal microscope (Leica) was used for observation. To visualize blood flow in mice, fluorescein isothiocyanate-conjugated dextran (MW 2,000,000) and tetramethylrhodamine-conjugated dextran (MW 2,000,000) (100 μl) were injected into the tail vein with a 29G syringe (Termo). To visualize mouse vasculature, Alexa™647-conjugated mouse-specific CD31 antibody (BD Biosciences Pharmingen) (100 μl) was injected from the tail vein.

3-3. Histochemical Staining

Removed tissues and the ears of wild-type C57BL/6J mice (Japan SLC) at respective developmental stages were fixed in 4% paraformaldehyde (PFA) (Wako)/phosphate buffer (PBS) (pH 7.4) at 4° C. for 2 hr. Then, tissues were washed with 100 mM ammonium chloride (Wako)/PBS at 4° C. for 10 min three times. After soaking in 15% sucrose (Wako)/PBS at 4° C. for 1 hr, tissues were left in 30% sucrose/PBS at 4° C. overnight. Then, the tissues were embedded in O.C.T. Compound (Sakura Japan) (30 ml). After leaving at 4° C. for 1 hr, the tissues were subjected to quick freezing with liquid nitrogen to thereby prepare frozen blocks. The resultant frozen blocks were sliced into 5 μm thick sections with cryostat HM 500 O (Zeiss) to prepare frozen tissue sections. The resultant tissue sections were subjected to Alcian blue staining (Muto Pure Chemicals) and Elastica van Gieson staining (Muto Pure Chemicals).

Alcian blue staining was performed as follows. Briefly, tissue sections were washed with 1×PBS (phosphate-buffered saline) to remove OCT Compound and then pre-treated with 3% aqueous acetic acid for 3 min, followed by staining with Alcian blue solution for 60 min. Stain solution was washed out with 3% aqueous acetic acid. After washing with pure water, tissue sections were nuclear-stained with Kernechtrot for 5 min. Excessive Kernechtrot was washed out with pure water. Subsequently, tissue sections were dehydrated with a series of ethanol bath of increasing concentration and cleared with xylene.

Elastica van Gieson staining was performed as follows. Briefly, after removal of OCT Compound, tissue sections were pre-treated with 1% hydrochloric acid/70% ethanol for 3 min and then soaked in Weigert's resorcin-fuchsin solution for 60 min. Stain solution was removed with 1% hydrochloric acid/70% ethanol. Then, tissue sections were nuclear-stained in Weigert's iron hematoxylin solution for 5 min. Saddening was performed with lukewarm water. Subsequently, tissue sections were soaked in van Gieson solution for 15 min, dehydrated with a series of ethanol bath of increasing concentration and cleared with xylene.

3-4. Immunohistochemical Staining

Removed tissues and the ears of wild-type C57BL/6J mice (Japan SLC) at respective developmental stages were fixed in 4% paraformaldehyde (PFA) (Wako)/phosphate buffer (PBS) (pH 7.4) at 4° C. for 2 hr. Then, they were washed with 100 mM ammonium chloride (Wako)/PBS at 4° C. for 10 min three times. Subsequently, they were left in 30% sucrose/PBS at 4° C. overnight and embedded in O.C.T. Compound (Sakura Japan) (30 ml). After leaving for 30 min, the tissues were subjected to quick freezing with liquid nitrogen to thereby prepare frozen blocks. The resultant frozen blocks were sliced into 5 μm thick sections with cryostat HM 500 O (Zeiss) to prepare frozen tissue sections. The resultant tissue sections were washed with 0.1% tween TBS to remove O.C.T. Compound. TBS-T around the frozen sections were wiped out. The targets of staining were marked with a water-repellent pen (Dako) in an enclosing manner to make them water-repellent. Subsequently, the tissues were blocked with Protein Block Serum-Free Ready-to-Use (Dako) at 4° C. for 24 hr. Primary antibodies were reacted at 4° C. overnight. After this treatment, the resultant tissues were washed with TBS-T for 5 min three times. Secondary antibodies were added dropwise and reacted at room temperature for 2 hr. After washing with TBS-T for 5 min three times, nuclear staining and inclusion were performed with DAPI-added FA Mounting Fluid (Becton Dickinson). For dilution of the primary and secondary antibodies, Protein Block Serum-Free Ready-to-Use (DAKO) was used.

As primary antibody, Alexa Fluor647 anti-mouse CD31 (Biolegend) (1:200), rabbit anti-polyclonal laminin (Dako) (1:200), mouse anti-mouse/human CD44 (Biolegend) (1:200), Rabbit anti-polyclonal Ki67 (Abcam) (1:200), rabbit anti-human Collagen type I (MONOSAN) (1:200) and mouse anti-chicken Collagen type II (CHEMICON) (1:200) were used.

As secondary antibody,
Alexa488 Goat Anti-mouse IgG1 (Molecular Probe) (1:500),
Alexa555 Goat Anti-rabbit IgG (Molecular Probe) (1:500),
Alexa555 Goat Anti-mouse IgG2b (Molecular Probe) (1:500),
Alexa555 rabbit Anti-rat IgG2b (Molecular Probe) (1:500) and
Alexa546 Goat Anti-rabbit IgG (Molecular Probe) (1:500) were used.

For observation, a fluorescence microscope (Zeiss) was used.

3-5. Isolation of Perichondrium Tissue and Cartilage Tissue from Human Ear Cartilage Ear elastic cartilage remnants from microtia patients were kindly supplied under the approval of the Ethics Committee of Yokohama City University (approval No. 03-074) and used in experiments.

The supplied human ear elastic cartilage was stereomicroscopically separated into two layers, the perichondrium tissue layer and the cartilage tissue layer.

3-6. Cultivation of Human Ear Perichondrocytes and Chondrocytes

The human ear elastic cartilage was stereomicroscopically separated into two layers, the perichondrium portion and the cartilage parenchyma portion, and dissected tissues were cut into small pieces. The resultant pieces were suspended and shaken in 0.2% Collagenase Type II (Worthington) to thereby decompose cartilage matrix and isolate cells. In the process, perichondrium tissue and perichondrium were shaken for 2 hr, whereas cartilage tissue was shaken for 10-15 hr. Cell suspensions of individual tissues were filtered with a 100 μm Cell Strainer (BD Falcon) and centrifuged (1500 rpm, 4° C., 5 min). After removal of the supernatant, cells were washed with standard medium [10% fetal bovine serum (FBS; Gibco)- and 1% antibiotic antimycotic solution (Sigma)-supplemented Dulbecco's Modified Eagle's Medium Nutrient Mixture F-12 HAM (D-MEM/F-12; Sigma)] and centrifuged (1500 rpm, 4° C., 5 min). Recovered individual cells were seeded on a 35 mm easy grip cell culture dish (Falcon) or a 60 mm cell culture dish (Falcon). Then, cells were cultured in an incubator with the gas phase conditions set at 37° C. and a $CO_2$ concentration of 5%.

Subculture of cells was performed with 0.2% Collagenase Type II (Worthington)-containing Dulbecco's modified Eagle medium and Ham's F-12 medium (D-MEM/F-12; Sigma). To medium-free dishes, the 0.2% collagenase solution mentioned above was added. Dishes were left stationary for 20 min in an incubator. Standard medium was added to the dishes, and cells were recovered by pipetting. The recovered cells were centrifuged (1500 rpm, 4° C., 5 min), washed, seeded on dishes and cultured again. When dishes reached confluence, the same passage operations were performed. These operations were repeated.

3-7. Cultivation of Human Umbilical Vein Endothelial Cells

Subculture of normal human umbilical vein endothelial cells (HUVEC) (Lonza) was performed as follows. Briefly, cells were washed with 1×PBS three times. One mL of 0.05% Tripysin-EDTA (Gibco) was poured over cells, which were then left stationary in an incubator for 1 min. After addition of Endothelial Cell Growth Medium Single Quots Supplements and Growth Factors (EGM) (Lonza), cells were recovered by pipetting. The recovered cells were centrifuged (950 rpm, 4° C., 5 min), washed, seeded on dishes and cultured again. When dishes reached confluence, the same passage operations were performed. These operations were repeated.

3-8. Fluorescence Labeling with Retrovirus Vectors

All the gene recombination experiments were performed in P2 level safety cabinets under approval of Gene Recombination Committee of Yokohama City University.

Production of virus vectors pGCDΔNsamEGFP and pGCDΔNsamKO was performed by the method described below. Briefly, 293GPG/pGCDΔNsamEGFP cells and 293GPG/pGCDΔNsamKO cells were seeded on poly-L- lysine-coated dishes and cultured in a custom-made medium (designated "293GPG medium"). Specifically, DMEM (Sigma) containing 10% fetal bovine serum (Gibco, USA), 2 mmol/L L-glutamine (Gibco), 1× penicillin/streptomycin (Gibco), 1 μg/mL tetracycline hydrochloride (SIGMA T-7660), 2 μg/mL puromycin (Sigma P-7255) and 0.3 mg/mL G418 (Sigma A-1720) was used. Cultivation was carried out in a 37° C., 10% $CO_2$ incubator. When cells reached about 80% confluence, the medium was exchanged with a medium prepared by removing tetracycline hydrochloride, puromycin and G418 from the 293GPG medium (and designated "293GP medium") (the day of exchange is written as day 0). After another medium exchange at day 3, the medium inclusive of the virus was recovered starting at day 4 and 293GP medium was filled again. The recovered medium was passed through a 0.45 μm filter and temporarily stored at 4° C. The medium recovered up to day 7 by the above-described procedures was centrifuged (6000×g, 4° C., 16 hr). To the resultant pellet, 400 μL of Stempro (Invitrogen) was added. After shaking at 4° C. for 72 hr, the resultant solution was recovered and stored at −80° C. (designated "100-fold concentrated virus solution").

Two types of cells (human ear perichondrocytes and HUVECs) were cultured until they reached 30-50% confluence. Protamine (Sigma) was added to each medium to give a final concentration of 0.4 μm/mL. To HUVEC, 100-fold concentrated virus solutions of pGCDΔNsamEGFP and pGCDΔNsamKO were added; to hMSC, 100-fold concentrated virus solution of pGCDΔNsamKO was added; and to hFLC, 100-fold concentrated virus solution of pGCDΔNsamEGFP was added. Then, cells were infected in a 37° C., 5% $CO_2$ incubator for 4 hr and washed with PBS twice. Medium was exchanged with fresh medium, followed by incubation in a 37° C., 5% $CO_2$ incubator. These operations were repeated four times. Then, the efficiency of viral vector introduction into each cell was calculated using FACS CANTO.

3-9. Comparison of Proliferative Capacities

Perichondrocytes were seeded at a density of $4.0 \times 10^4$ cells/cm² and cultured in a growth medium. After 24 hours, cell culture inserts (BD Falcon) plated with perichondrocytes and HUVECs each at a density of $4.0 \times 10^4$ cells/mL were inserted. After 12 day cultivation, one drop of Nuc Blue Live Cell Stain (Molecular Probes) was added to the medium. Cells were left stationary in an incubator for 10 min, followed by determination of cell count with IN Cell Analyzer 2000 (GE). In this study, Standard medium [10% fetal bovine serum (FBS; Gibco)- and 1% antibiotic antimycotic solution (Sigma)-supplemented Dulbecco's Modified Eagle's Medium Nutrient Mixture F-12 HAM (D-MEM/F-12; Sigma)] was used as a growth medium.

3-10. Analysis of Cell Surface Antigens with FACS

Perichondrocytes were seeded at a density of $1.0 \times 10^5$ cells/mL and cultured in a growth medium. After 24 hours, cell culture inserts (BD Falcon) plated with perichondrocytes and vascular endothelial cells each at a density of $7.5 \times 10^4$ cells/mL were inserted. After 3 day cultivation, 0.2% collagenase solution mentioned above was added to medium-free dishes, which were then left stationary in an incubator for 20 min. Standard medium was added to dishes, and cells were recovered by pipetting.

Cells were stained on ice for 30 min using fluorescein isothiocyanate (FITC)-, phycoerythrin (PE)- and allophycocyanin (APC)-conjugated monoclonal antibodies for each type of cells. After washing three times, cells were suspended in 1 μg/ml propidium iodide (PI)-containing PBS and subjected to analysis with FACS. For the analysis, MoFlo cell sorter (DakoCytomation) was used. Sorting was performed on perichondrocytes using fluorescent-conjugated mouse anti-human CD44 and CD90 (both from BD Science). In the process of sorting, cell debris, dead cells and tablets were removed with forward-scattered light, side-scattered light and PI.

3-11. Cartilage Reconstruction by Conventional Method

Ear perichondrocytes were differentiated into chondrocytes by layered cultivation. Perichondrocytes were prepared to give a density of $2.5 \times 10^4$ cells/cm² and seeded on cell culture dishes (Falcon). For 2 days after seeding, cells were cultured in Standard medium to promote cell adhesion. Subsequently, cells were cultured in a cartilage differentiation inducing medium for 5 days. This medium is D-MEM/F-12 medium (Sigma) supplemented with 10% FBS (Gibco), 1% antibiotic antimycotic solution, L-ascorbic acid 2-phosphate (Wako), dexamethasone (Sigma), insulin growth factor-I (Sigma) and basic fibroblast growth factor (Kaken Pharmaceutical). After 7 day cultivation using this differentiation inducing medium, separately provided cells were adjusted to a density of $5 \times 10^4$ cells/cm² and seeded on the medium from above to form a second layer. After seeding the second layer, cells were cultured in Standard medium for 2 days in the same manner as the first layer. Subsequently, 5 day cultivation was performed in the cartilage differentiation inducing medium. These procedures were repeated again to thereby yield a 3-layered culture. All cultivation of cells was performed in an incubator with the gas phase conditions set at 37° C. and a $CO_2$ concentration of 5%. Each type of differentiated cells was scraped off with a cell scraper (Iwaki), transplanted into cranial windows and observed under a confocal microscope.

3-12. Induction of Three-Dimensional Organization

EGM and Matrigel (150 μm each) were added separately to 24-well plates, which were then left stationary in an incubator for 30 min. Cell suspensions ($1.0 \times 10^5$ cells/ml each) of perichondrocytes and HUVEC were mixed and centrifuged (950 rpm, 4° C., 5 min). Recovered cells were placed in a small amount of growth medium and seeded on the wells. After the cells were left stationary for 5-20 min, 1 mL of a medium prepared by removing EGF from Endothelial Cell Growth Medium SingleQuots Supplements and Growth Factors (EGM) (and designated as EGM-ΔEGF) (Lonza) was added to the well. Cells were cultured for 3 days while EGM was exchanged every other day. Cultivation was performed using Standard Medium [10% fetal bovine serum (FBS; Gibco)- and 1% antibiotic antimycotic solution (Sigma)-supplemented Dulbeccos Modified Eagle's Medium Nutrient Mixture F-12 HAM (D-MEM/F-12; Sigma)].

The thus induced three-dimensional tissues were transplanted into cranial windows and subjected to live imaging with the eye and confocal microscope. Further, the tissues were taken out at days 15, 30 and 60 of transplantation and subjected to histochemical staining.

A nanomesh (pore size=0.45 μm) was placed on the brain of cranial window mice in order to inhibit blood perfusion into transplant, and cells were transplanted onto the nanomesh.

3-14. Quantification of Alcian Blue-Positive Area

Images of the entire tissue of Alcian blue-stained tissue sections were obtained with HS all-in-one fluorescence microscope (Keyence) and positive areas were quantified with Image J (http://rsb.info.nih.gov/ij/)[42].

3-15. Statistical Analysis

Data are shown as the mean±s.d. obtained from experiments using at least three independent specimens. For statistical analysis, first, 3 or 4 groups were analysed using the Kruskal Wallis-H test. When found P<0.01, multiple comparison test was performed using Mann-Whitney's U test with Bonferroni correction. When P value satisfied P<0.001 or P<0.01, the result was found to have a statistically significant difference.

4. Results 4-1. Tracking-Type Fixed Point Observation of Chondrogenetic Processes Ear cartilage of E17.5 EGFP transgenic mouse was transplanted into the cranial window. Processes of differentiation from CPCs into mature chondrocytes were observed in a tracking manner by live imaging with confocal microscope. Macroscopic observations confirmed that anastomosis of transplant blood vessels and host mouse blood vessels was beginning to occur at day 1 or 2 of transplantation. However, at day 5 and thereafter, it was confirmed that blood vessels were completely anastomosed. From day 5, blood vessels gradually regressed until they disappeared almost completely from the transplant at day 11 (FIG. 2A). Visualization of mouse endothelial cells and blood flow by intravascular administration of tetramethylrhodamine-conjugated dextran and Alexa647-conjugated mouse specific CD31 (mCD31) antibody confirmed that at day 3 of transplantation, vessels with blood flow had invaded into the transplanted ear cartilage. At day 7, vascular network had regressed, leaving only part of vascular endothelial cells (FIG. 2B). At the same time, circular CPCs had changed into a cobblestone-like shape resembling chondrocytes. At day 10, blood vessels had completely regressed from the transplanted ear cartilage (FIG. 2B). At day 20, perichondrium tissues with blood vessels encapsulating cartilage tissue were formed; cells constituting the cartilage tissue presented a cobblestone-like shape (FIG. 2B). Prior studies have revealed the presence of CPCs with high cartilage differentiation capacities in ear perichondral tissues of both adult humans and mice. To determine whether ear cartilage transplants at day 20 after transplantation would form elastic cartilage or not, histochemical analysis was conducted. The results of Alcian blue staining showed the formation of proteoglycan-producing cartilage tissue and the results of Elastica van Gieson staining (which stains elastic fiber) showed the formation of elastic cartilage (FIG. 2C). The transplanted ear cartilage of early developmental stage could be macroscopically verified to grow starting at day 5 of transplantation when vascular regression began to occur (FIG. 2A).

4-2. Transient Vascularization in Mouse Ear Cartilage of Early Developmental Stage Frozen tissue sections were prepared with a cryostat from ear cartilage samples at developmental stages of E18.5, P0, P2, P10 and P30 and subjected to immunohistochemical staining against laminin, or a component protein of matrix membrane supporting vascular endothelial cells, and the vascular endothelial cell marker mCD31. At the stage of E18.5, cells expressing laminin and mCD31 were present at the site destined for chondrogenesis. At P0, more blood vessels were present than at E18.5; a maximum number of blood vessels were observed at P2. On the other hand, blood vessels were slightly observable at P10 and no blood vessels were observable at P30 (FIG. 3A). Distances between laminin and mCD31-expressing blood vessels and CPCs were measured at the stages of P0, P2, P10 and P30. As it turned out, the distance measured the shortest (17.8 μm) at P2 (FIG. 3B).

4-3. Transient Vascularization in Conventional Cartilage Reconstruction Method

Examination was made to see whether vascularization also occurs in cartilage reconstruction process. Using a growth factor-containing differentiation medium, layered cultivation was conducted to induce CPCs to differentiate into cartilage. When the culture supernatant became slightly viscous, cells were recovered with a cell scraper, pelleted and transplanted into cranial windows (FIG. 4A). Fluorescent-conjugated dextran was administered to host mice intravascularly to visualize blood flow. At day 10 of transplantation, blood vessels invaded into the transplanted pellet and remained there until day 30. At day 60, blood vessels had completely regressed from the transplanted pellet (FIG. 4B). Examination by histological analysis was made to see whether CPCs had differentiated into mature chondrocytes or not. The results revealed that at day 10 of transplantation when blood vessels had invaded, Alcian blue staining was negative whereas at day 30 of transplantation, a slightly blue color was observed. At day 60 when blood vessels had completely regressed, cells were stained in dark blue color, showing that CPCs had differentiated into proteoglycan-producing mature chondrocytes.

4-4. Effect of Vascular Endothelial Cells on the Proliferative Capacity of CPCs

The inventors examined whether cells were proliferating or not in ear cartilage of early developmental stages where invasion of blood vessels occurs. Using ear cartilage samples of P0 and P2 (where invasion of blood vessels occurred) and P30 (where blood vessels completely regressed), immunohistochemical staining was performed against Ki67 and CD44. Proliferating CPCs were observed by focusing on CD44[43] (which we have reported as a CPC specific marker) and the cell growth marker Ki67. At stages P0 and P2 where blood vessels were invading, Ki67-positive cells could be observed. At P2 where blood vessel invasion was highest, the largest number of Ki67-positive cells could be observed. At P30 where blood vessels had regressed, Ki67-positive cells could not be observed (FIG. 5). Subsequently, CPCs were seeded at a low density and co-cultured with normal human umbilical vascular endothelial cells (HUVECs) in a Transwell system to evaluate the effect of vascular endothelial cells on the proliferative capacity of CPCs. As control, co-cultivation with mesenchymal stem cells, fibroblasts or chondrocytes was performed. At day 12 of co-cultivation, CPCs co-cultured with HUVECs became so dense as to reach nearly 100% confluence. Cell counts were determined with In Cell Analyzer. As it turned out, the cell count of CPCs cultured alone was approximately 2500 cells/cm$^2$ whereas the cell count of CPCs co-cultured with HUVECs was approximately 4000 cells/cm$^2$. Co-cultivation with mesenchymal stem cells, fibroblasts or chondrocytes showed no effect on the proliferative capacity of CPCs (FIG. 6A). Subsequently, changes in the cell surface antigens caused by co-cultivation were analyzed by flow cytometry. In prior studies, the inventors identified CD44$^+$ CD90$^+$ cells as human CPCs. At day 12 of co-culture with endothelial cells, CD44$^+$ CD90$^+$ cells occupied 0.79% of total cells in control (CPCs alone) while CD44$^+$ CD90$^+$ cells increased to 12.44% as a result of co-culture with HUVECs (FIG. 6B).

4-5. Three-Dimensional Organization of CPCs by Co-culture with Vascular Endothelial Cells The present inventors have developed a three-dimensional culture system by recapitulating interactions between CPCs and endothelial cells; this culture system does not use scaffold materials or growth factors. When human CPCs and HUVECs were co-cultured on Matrigel, cells began to aggregate gradually 12 hours after seeding and formed three-dimensional structures about 3 mm in diameter in a self-driven manner 48 hours after seeding (FIG. 7A). These three-dimensional tissues had a certain amount of mechanical strength. Therefore, they could be transplanted into mouse cranial windows by dipping up with a spatula, without deformation of their shapes. As in the case where E17.5 mouse immature ear cartilage was transplanted, blood flow was macroscopically shown to start invading again into transplants at day 3 of transplantation. At day 10 of transplantation, it could be confirmed that HUVECs and mouse blood vessels were completely anastomosed to thereby construct a vascular network within the transplant; thus, transient vascularization could be recapitulated (FIG. 7B). Tracking observation of vascularized sites revealed that at day 30 of transplantation, the vascular network completely disappeared and CPCs metamorphosed to a cobblestone-like shape similar to that of chondrocytes, suggesting that CPCs differentiated into mature chondrocytes. Live imaging analyses also confirmed that at day 3 of transplantation, HUVECs constructed a vascular network which regressed completely at day 30 of transplantation. Histological analysis was conducted to examine whether the transplanted three-dimensional tissues formed cartilage tissues or not. At day 3 of transplantation when blood vessels were invading, Alcian blue staining was negative but the transplant was partly stained in blue at day 15 of transplantation. At day 30 when blood vessels completely regressed, part of the transplant was stained in dark blue; and at day 60 of transplantation, most of the transplanted three-dimensional tissues were stained in dark blue by Alcian blue staining (FIG. 7C). From these results, it was confirmed that the three-dimensional tissues constructed by co-culture of CPCs and HUVECs formed proteoglycan-producing cartilage tissues. Further, cartilage reconstruction was also confirmed by safranin O staining performed at day 30 of transplantation; it was confirmed by Elastica van Gieson staining that the formed cartilage was elastic cartilage. Immunohistochemical staining showed that the reconstructed cartilage had a collagen I-positive perichondral tissue encapsulating aggrecan-positive cartilage tissue. Further, immunohistochemical staining of hCD31 showed the presence of vascular endothelial cells in the reconstructed perichondral tissue (FIG. 7D).

Dedifferentiated chondrocytes were co-cultured with human umbilical vascular endothelial cells (HUVECs) in the same three-dimensional culture system. As in the case where CPCs were used, reconstruction of elastic cartilage was confirmed by Alcian blue staining and Elastica van Gieson staining (FIG. 7E).

4-6. Inhibition of Chondrogenesis Using Blood Flow-Blocked Transplantation Model To elucidate whether mouse-derived blood vessels and blood perfusion are essential for maturation of cartilage or not, a blood flow-blocked transplantation model was established in which a nanomesh (pore size: 0.45 μm) was placed between the three-dimensional tissues constructed by co-culturing CPCs and HUVECs and the mouse brain so that the mouse blood flow would not act on the transplant (FIG. 8A). It was confirmed that no blood flow was present around the transplanted three-dimensional tissues even at day 15 of transplantation (FIG. 8B). Live imaging showed that a large number of HUVECs were present at day 3 of transplantation; HUVECs decreased at day 7 of transplantation; and most of the HUVECs were dead at day 10 of transplantation. Further, as HUVECs decreased, CPCs per se died out at day 11 of transplantation (FIG. 8C). Thus, it was shown that CPCs failed to engraft as a result of blocking blood perfusion. Further, immunohistochemical staining showed that in the blood perfusion-blocked three-dimensional tissues at day 15 of transplantation, collagen II (cartilage substrate) was negative and caspase3 (central enzyme in apoptosis process) was positive (FIG. 8D). On the other hand, when blood perfusion was not blocked, caspase3-positive cells were not detected, and collagen II-positive cartilage tissue was formed.

4-7. Comparison with Conventional Methods in terms of Elastic Cartilage Reconstruction Capacity In order to compare cartilage reconstruction efficiencies between the conventional pellet transplantation[44] and the transplantation of three-dimensional tissues constructed by co-culturing CPCs with HUVECs, three-dimensional tissues thus constructed were transplanted into the left cerebral hemisphere of a cranial window mouse and a pellet was transplanted into the right cerebral hemisphere of the same cranial window mouse (FIG. 9A). In Alcian blue staining conducted at day 10 of transplantation, the pellet was not stained in blue whereas the three-dimensional tissues constructed by co-culturing were stained in blue. These results suggested that co-cultivation with HUVECs allows highly efficient differentiation of CPCs into proteoglycan-producing mature chondrocytes. At day 30 of transplantation, the three-dimensional tissues constructed by co-cultivation were seen to form cartilage tissues producing large amounts of proteoglycan. At day 60 of transplantation, most of the three-dimensional tissues constructed by co-cultivation were stained in dark blue by Alcian staining, confirming the formation of terminally differentiated mature cartilage tissues. In contrast, in the conventional pellet transplantation, only a part of the pellet formed proteoglycan-producing cartilage tissues (FIG. 9A). These results show that CPCs co-cultured with HUVECs reconstruct cartilage more efficiently. To quantify Alcian blue-positive regions, the sites stained in blue were extracted with Image J and their areas were measured (FIG. 9B). In the three-dimensional tissues constructed by co-cultivation of CPCs and HUVECs, the Alcian blue-positive area was approximately 100,000 $\mu m^2$ at day 10 of transplantation, approximately 130,000 $\mu m^2$ at day 30 and approximately 250,000 $\mu m^2$ at day 60. On the other hand, in the conventional pellet transplantation, the transplanted pellet produced cartilage tissues of the following areas: approximately 35,000 $\mu m^2$ at day 10 of transplantation, approximately 20,000 $\mu m^2$ at day 30 and approximately 80,000 $\mu m^2$ at day 60. Comparison of these results showed that the three-dimensional tissues constructed by co-cultivation formed cartilage tissues with areas that were 2.85 times larger at day 10 of transplantation, 6.5 times larger at day 30, and 3.27 times larger at day 60 (FIG. 9C).

5. Discussion

Cartilage tissue is a supporting organ consisting of chondrocytes and extracellular matrix surrounding the chondrocytes. The cell stroma of cartilage tissue differs from other supporting tissues such as connective tissue or bone tissue in that it does not contain blood vessels, lymphatic vessels, nerves and the like[45,46]. Therefore, compared to solid organs with complex higher structures, cartilage is an area where early realization of regenerative therapy is expected[47,48]. In the present study, the inventors have found by tracking observation of chondrogenesis via live imaging that blood vessels (which have been considered unnecessary) transiently invade in the differentiation process of CPCs. Transplanted ear cartilage at an early developmental stage swelled immediately after the blood vessel invasion, suggesting rapid proliferation of CPCs. In ear cartilage at the time of blood vessel invasion, there were observed cells that expressed CD44 (reportedly a specific marker for mesenchymal stem cells) and some of those cells were found Ki67-positive. Then, the inventors co-cultured CPCs and vascular endothelial cells and found enhanced proliferation of $CD44^+$ $CD90^+$ cells (which are CPCs).

It is becoming clear that blood vessels not only supply oxygen and nutrients and remove waste products but also play an important role in constructing higher structures[49-52]. For example, with respect to interactions between vascular endothelial cells and hepatocytes in the liver, it is known that lacking of angiogenesis inhibits morphogenesis of the liver in VEGFR2 (Vascular Endothelial Growth Factor Receptor-2) knockout mice. However, interactions with vascular endothelial cells that might occur when an avascular tissue such as cartilage tissue is developing are totally unknown. It has been suggested that vascular endothelial cells, although they regress as the development of cartilage proceeds, are capable of promoting the inherent capacity of CPCs to differentiate into cartilage without using growth factors. When used clinically, growth factors present some problems in terms of cost and safety. Therefore, the technique of the present invention which performs co-culturing of CPCs with endothelial vascular cells to enable construction of cartilage tissue from chondrocytes without using growth factors has a potential to become a technique that offers great benefits toward clinical application.

In clinical application, control of the morphology of transplanted/reconstructed tissues also raises a problem. For preparing human cartilage tissue by conventional tissue engineering techniques, scaffolds have been considered necessary. Many of scaffolds are composed of biological materials or synthetic polymers. However, scaffolds for preparing human cartilage tissues that can withstand use in clinical applications have not been developed to date. There have been developed methods in which chondrocytes differentiated into cartilage are directly injected, together with a gel-like matrix, under the skin of patients; or such chondrocytes are first transplanted under the skin of the abdomen and the reconstructed cartilage-like tissue is transplanted secondarily. In any of these methods, however, regenerated cartilage cannot be obtained in a consistent manner. In the present study, the inventors have shown that CPCs, if co-cultured with vascular endothelial cells, are capable of inducing three-dimensional tissues in vitro in a self-driven manner without using scaffold materials. This three-dimensional tissue has a sufficient mechanical strength to be transplanted without deformation of its shape, so it would be easy to control its morphology during transplantation.

Many of the conventional methods of inducing the differentiation of mesenchymal stem cells into cartilage are extremely low in efficiency for several reasons including low engraftment ratios and the terminally differentiated chondrocytes that can be obtained account for only 10-20% of the transplanted cell count. According to the method for generating elastic cartilage established in the present study, the efficiency of inducing terminal differentiation is greatly increased, so it is expected that efficient reconstruction of large-sized elastic cartilage (compared to that obtained in conventional methods) will become possible. Reconstruction of large-sized elastic cartilage with a complex morphology, such as ear cartilage, is demanded. At present, the inventors are examining whether it would be possible to create a large sized elastic cartilage by the mass subcutaneous transplantation into mice of three-dimensional tissues constructed by interacting human CPCs with vascular endothelial cells.

For clinical application of the method for generating elastic cartilage established in the present study, autologous cartilage is not sufficient and it is necessary to construct a system that is capable of consistent supply of HLA (human leukocyte antigen)-matched vascular endothelial cells. HLA acts as an important molecule involved in human immunity. When a patient has received a cell or organ transplant from a donor of different HLA type, immunorejection occurs. Therefore, it is necessary to use HLA-matched transplants as much as possible. For this purpose, establishment of vascular endothelial cell banks is necessary which collect, culture and preserve vascular endothelial cells from umbilical cords. Although umbilical cord is a biological resource that has been abandoned to date, it would be capable of consistent supply of vascular endothelial cells if it could be preserved like umbilical cord blood. If a patient's HLA-matched vascular endothelial cells and CPCs collected/cultured in a minimally invasive manner were co-cultured to induce three-dimensional organization and the resultant three-dimensional tissues were transplanted, a novel method could be provided for treating craniofacial tissue deformations resulting from congenital defects or traumas.

In future, it is desired that cartilage tissues be reconstructed three-dimensionally in vitro. As a three-dimensional cultivation method that recently attracted researchers' attention, a method which mimics a micro gravity environment by using a rotating reactor called rotating wall vessel (RWV) bioreactor may be given. In a prior study, the inventors reconstructed cartilage-like tissue by using an RWV bioreactor and combining human ear perichondrocytes and a small-sized novel scaffold[53]. In fact, however, a problem concerning the strength of cartilage-like tissue remained to be solved. Then, by combining RWV with the unique approach of recapitulating the vascularization occurring in the process of chondrogenesis, terminal cartilage differentiation induction in vitro which has been difficult to achieve by conventional cultivation techniques is expected to materialize.

CPCs present in ear perichondrium have a capacity to differentiate into hyaline cartilage, a different type of cartilage tissue. It has been revealed that articular cartilage tissue can be reconstructed by transplanting such CPCs (data unpublished). Since the technique of the present invention efficiently generates cartilage by recapitulating transient vascularization, it is capable of resolving the problem that the post-transplantation efficiency of cartilage reconstruction is low in the regenerative therapy on articular cartilage deficiencies. Once articular cartilage is damaged, the damage proceeds to secondary degenerative diseases such as arthritis or knee osteoarthritis since articular cartilage does not have a healing capacity. It is estimated that the number of patients with knee osteoarthritis amounts to 25,300,000 in Japan alone. There are indeed a considerably large number of patients who need be treated. It is expected that a new method for treating articular cartilage deficiency in such a great need will be provided by co-culturing vascular endothelial cells with CPCs present in perichondrium that can be collected in a minimally invasive manner, inducing three-dimensional organization and transplanting the resultant three-dimensional tissue.

6. References

1. Chang, S. C., Tobias, G., Roy, A. K., Vacanti, C. A. & Bonassar, L. J. Tissue engineering of autologous cartilage for craniofacial reconstruction by injection molding. Plast Reconstr Surg 112, 793-799; discussion 800-791 (2003).
2. Beahm, E. K. & Walton, R. L. Auricular reconstruction for microtia: part I. Anatomy, embryology, and clinical evaluation. Plast Reconstr Surg 109, 2473-2482; quiz following 2482 (2002).
3. Firmin, F., Sanger, C. & O'Toole, G. Ear reconstruction following severe complications of otoplasty. J Plast Reconstr Aesthet Surg (2008).
4. Kline, R. M., Jr. & Wolfe, S. A. Complications associated with the harvesting of cranial bone grafts. Plast Reconstr Surg 95, 5-13; discussion 14-20 (1995).
5. Laurie, S. W., Kaban, L. B., Mulliken, J. B. & Murray, J. E. Donor-site morbidity after harvesting rib and iliac bone. Plast Reconstr Surg 73, 933-938 (1984)
6. Skouteris, C. A. & Sotereanos, G. C. Donor site morbidity following harvesting of autogenous rib grafts. J Oral Maxillofac Surg 47, 808-812 (1989).
7. Whitaker, L. A., et al. Combined report of problems and complications in 793 craniofacial operations. Plast Reconstr Surg 64, 198-203 (1979).
8. Eppley, B. L. & Dadvand, B. Injectable soft-tissue fillers: clinical overview. Plast Reconstr Surg 118, 98e-106e (2006).
9. Matton, G., Anseeuw, A. & De Keyser, F. The history of injectable biomaterials and the biology of collagen. Aesthetic Plast Surg 9, 133-140 (1985).
10. Nagata, S. Modification of the stages in total reconstruction of the auricle: Part I. Grafting the three-dimensional costal cartilage framework for lobule-type microtia. Plast Reconstr Surg 93, 221-230; discussion 267-228 (1994).
11. Maas, C. S., Monhian, N. & Shah, S. B. Implants in rhinoplasty. Facial Plast Surg 13, 279-290 (1997).
12. Matarasso, A., Elias, A. C. & Elias, R. L. Labial incompetence: a marker for progressive bone resorption in silastic chin augmentation. Plast Reconstr Surg 98, 1007-1014; discussion 1015 (1996).
13. Zeng, Y., Wu, W., Yu, H., Yang, J. & Chen, G. Silicone implants in augmentation rhinoplasty. Aesthetic Plast Surg 26, 85-88 (2002).
14. Berry, L., Grant, M. E., McClure, J. & Rooney, P. Bone-marrow-derived chondrogenesis in vitro. J Cell Sci 101 (Pt 2), 333-342 (1992).
15. Ma, H. L., Hung, S. C., Lin, S. Y., Chen, Y. L. & Lo, W. H. Chondrogenesis of human mesenchymal stem cells encapsulated in alginate beads. J Biomed Mater Res A 64, 273-281 (2003).
16. Terada, S., Fuchs, J. R., Yoshimoto, H., Fauza, D. O. & Vacanti, J. P. In vitro cartilage regeneration from proliferated adult elastic chondrocytes. Ann Plast Surg 55, 196-201 (2005).
17. Goessler, U. R. et al. Tissue engineering in head and neck reconstructive surgery: what type of tissue do we need? Eur Arch Otorhinolaryngol 264, 1343-1356, (2007).
18. Caplan, A. I. Review: mesenchymal stem cells: cell-based reconstructive therapy in orthopedics. Tissue Eng 11, 1198-1211, (2005).
19. Shieh, S. J., Terada, S. & Vacanti, J. P. Tissue engineering auricular reconstruction: in vitro and in vivo studies. Biomaterials 25, 1545-1557 (2004).
20. Togo, T., et al. Identification of cartilage progenitor cells in the adult ear perichondrium: utilization for cartilage reconstruction. Lab Invest 86, 445-457 (2006).
21. Dickhut, A., et al. Calcification or dedifferentiation: requirement to lock mesenchymal stem cells in a desired differentiation stage. J Cell Physiol 219, 219-226 (2009).
22. Afizah, H., Yang, Z., Hui, J. H., Ouyang, H. W. & Lee, E. H. A comparison between the chondrogenic potential of human bone marrow stem cells (BMSCs) and adipose-derived stem cells (ADSCs) taken from the same donors. Tissue Eng 13, 659-666 (2007).
23. Koga, H., et al. Comparison of mesenchymal tissues-derived stem cells for in vivo chondrogenesis: suitable conditions for cell therapy of cartilage defects in rabbit. Cell Tissue Res 333, 207-215 (2008).
24. Sakaguchi, Y., Sekiya, I., Yagishita, K. & Muneta, T. Comparison of human stem cells derived from various mesenchymal tissues: superiority of synovium as a cell source. Arthritis Rheum 52, 2521-2529 (2005).
25. Kobayashi, S. et al. Presence of cartilage stem/progenitor cells in adult mice auricular perichondrium. PLoS One 6, e26393, (2011).
26. Kobayashi, S. et al. Reconstruction of human elastic cartilage by a CD44+ CD90+ stem cell in the ear perichondrium. Proc Natl Acad Sci USA 108, 14479-14484, (2011).
27. Gospodarowicz D, Weseman J, Moran J. Presence in brain of a mitogenic agent promoting proliferation of myoblasts in low density culture. Nature 256, 216-219, (1975)
28. Klagsbrun M, Langer R, Levenson R, Smith S, Lillehei C. The stimulation of DNA synthesis and cell division in chondrocytes and 3T3 cells by a growth factor isolated from cartilage. Exp Cell Res 105, 99-108, (1977)
29. Shiang R, Thompson L M, Zhu Y Z, Church D M, Fielder T J, Bocian M, Winokur S T, Wasmuth J J. Mutations in the transmembrane domain of FGFR3 cause the most common genetic form of dwarfism, achondroplasia. Cell 29, 335-342, (1994)
30. Deng C, Wynshaw-Boris A, Zhou F, Kuo A, Leder P. Fibroblast growth factor receptor 3 is a negative regulator of bone growth. Cell 22, 911-921, (1996)
31. Serra R, Johnson M, Filvaroff E H, LaBorde J, Sheehan D M, Derynck R, Moses H L. Expression of a truncated, kinase-defective TGF-beta type II receptor in mouse skeletal tissue promotes terminal chondrocyte differentiation and osteoarthritis. J Cell Biol 20, 541-552, (1997)
32. Furumatsu, T. et al. Smad3 induces chondrogenesis through the activation of SOX9 via CREB-binding protein/p300 recruitment. J. Biol. Chem 280, 8343-8350, (2005)
33. Garcia-Ramirez, M., Toran, N., Andaluz, P., Carrascosa, A. & Audi, L. Vascular endothelial growth factor is expressed in human fetal growth cartilage. J Bone Miner Res 15, 534-540, (2000).
34. Gerber, H. P. et al. VEGF couples hypertrophic cartilage remodeling, ossification and angiogenesis during endochondral bone formation. Nature medicine 5, 623-628, (1999).
35. Furukawa, T., Eyre, D. R., Koide, S. & Glimcher, M. J. Biochemical studies on repair cartilage resurfacing experimental defects in the rabbit knee. J Bone Joint Surg Am 62, 79-89, (1980).
36. L. Danisovic, P. Lesny, V. Havlas, P. Teyssler, Z. Syrova, M. Kopani, G. Fujerikova, T. Trc, E. Sykova, P. Jendelova. Chondrogenic differentiation of human bone marrow and adipose tissue-derived mesenchymal stem cells. J. Appl. Biomed 5, 139-150, (2007)
37. Havlas V, Kos P, Jendelová P, Lesný P, Trc T, Syková E. Comparison of chondrogenic differentiation of adipose tissue-derived mesenchymal stem cells with cultured chondrocytes and bone marrow mesenchymal stem cells. Acta Chir. Orthop. Traumatol. Cech 78, 138-144, (2011)

38. K. H. Park, K. Na. Effect of growth factors on chondrogenic differentiation of rabbit mesenchymal cells embedded in injectable hydrogels. J. Biosci. Bioeng 106, 74-79, (2008)
39. Yuan F. Jain R K et al. Vascular permeability and microcirculation of gliomas and mammary carcinomas transplanted in rat and mouse cranial windows. Cancer Res 54, 4564-8, (1994)
40. Koike, N. et al. Tissue engineering: creation of long-lasting blood vessels. Nature 428, 138-139, (2004).
41. Takebe, T. et al. Generation of functional human vascular network. Transplant Proc 44, 1130-1133, (2012).
42. Horvatic, I. et al. Prognostic significance of glomerular and tubulointerstitial morphometry in idiopathic membranous nephropathy. Pathol Res Pract 208, 662-667, (2012).
43. Aruffo, A., Stamenkovic, I., Melnick, M., Underhill, C. B. & Seed, B. CD44 is the principal cell surface receptor for hyaluronate. Cell 61, 1303-1313, (1990).
44. Wang, Y., Kim, U. J., Blasioli, D. J., Kim, H. J. & Kaplan, D. L. In vitro cartilage tissue engineering with 3D porous aqueous-derived silk scaffolds and mesenchymal stem cells. Biomaterials 26, 7082-7094, (2005).
45. Newman A P. Articular cartilage repair. Am J Sports Med 26, 309-324(1998)
46. Hollander, A. P., Dickinson, S. C. & Kafienah, W. Stem cells and cartilage development: complexities of a simple tissue. Stem Cells 28, 1992-1996, (2010).
47. Langer, R. & Vacanti, J. P. Tissue engineering. Science 260, 920-926, (1993).
48. Khademhosseini, A., Vacanti, J. P. & Langer, R. Progress in tissue engineering. Sci Am 300, 64-71, (2009).
49. Ding, B. S. et al. Inductive angiocrine signals from sinusoidal endothelium are required for liver regeneration. Nature 468, 310-315, (2010).
50. Ding, B. S. et al. Endothelial-derived angiocrine signals induce and sustain regenerative lung alveolarization. Cell 147, 539-553, (2011).
51. Lammert, E., Cleaver, O. & Melton, D. Role of endothelial cells in early pancreas and liver development. Mech Dev 120, 59-64, (2003).
52. Matsumoto, K., Yoshitomi, H., Rossant, J. & Zaret, K. S. Liver organogenesis promoted by endothelial cells prior to vascular function. Science 294, 559-563, (2001).
53. Takebe, T. et al. Human elastic cartilage engineering from cartilage progenitor cells using rotating wall vessel bioreactor. Transplant Proc 44, 1158-1161, (2012).

Example 2 Cultivation on Gels with Different Hardness

Perichondrocytes ($3\times10^6$) and vascular endothelial cells ($1\times10^6$) collected and subcultured in Example 1 were cultured under the same conditions as in Example 1 on a gel with a hardness of 0.5 kPa (hydrogel for cell cultivation; sample plate for evaluation (VERITAS)). The states of three-dimensional tissue formation at days 0, 1 and 2 of culture are shown in FIG. 10.

Using a hydrogel for cell cultivation and sample plates for evaluation (VERITAS), cells were seeded on the gel with a hardness of 0.2-50 kPa. The results are shown in FIG. 11. As a conventional culture dish, 10 cm easy grip cell culture dish (Falcon) was used.

When plates with a hardness of 0.5-25 kPa were used, perichondrocytes satisfactorily formed three-dimensional tissues capable of withstanding transplantation operations. When conventional culture dishes were used, cells failed to form three-dimensional tissues.

Example 3 Cultivation on Plates with a Shape in which Cells Gather in the Bottom Perichondrocytes ($3\times10^4$) and vascular endothelial cells ($1\times10^4$) were cultured on Prime Surface 96-well cell culture substrate having a U-shaped bottom (Sumitomo Bakelite) (FIG. 12A). For cultivation of three-dimensional tissues, a medium for inducing differentiation into cartilage was used. This medium is D-MEM/F-12 medium (Sigma) supplemented with 10% FBS (Gibco), 1% antibiotic antimycotic solution, L-ascorbic acid 2-phosphate (Wako), dexamethasone (Sigma), insulin growth factor-I (Sigma) and basic fibroblast growth factor (Kaken Pharmaceutical). The states of three-dimensional tissue formation at day 0 and day 2 of culture are shown in FIG. 12B. The seeded perichondrocytes autonomously began to aggregate and formed spherical, three-dimensional tissues with an approximate size of 400 μm the day after the seeding. These tissues could be easily recovered by pipetting or the like without deformation of their shapes.

Example 4 Subcutaneous Mass Transplantation

One hundred (100) three-dimensional tissues 4 mm in size formed by co-culturing perichondrocytes ($3\times10^6$) and vascular endothelial cells ($1\times10^6$) on Matrigel (BD) in the same manner as in Example 1 were recovered with a spatula and subcutaneously transplanted into NOD SCID mice (Sankyo Lab.) The states of transplantation are shown in FIG. 13. FIG. 13A shows the state in which a large amount of three-dimensional tissues are located subcutaneously. FIG. 13B shows approximately 30 three-dimensional tissues being recovered with a spatula.

Example 5 Transplantation into Deficient Site of Articular Cartilage

Six hundred (600) three-dimensional tissues 400 μm in size formed from perichondrocytes ($3\times10^4$) and vascular endothelial cells ($1\times10^4$) in the same manner as in Example 3 were transplanted into a deficient site of cartilage 3 mm in size that had been made in the surface of articular cartilage in an immunodeficient rat (CLEA Japan). The state is shown in FIG. 14. FIG. 14A shows the transplantation of three-dimensional tissues (approx. 400 μm) recovered in a large quantity into the deficient site with a pipette. FIG. 14B shows the deficient site in articular cartilage immediately after transplantation. After transplantation, the site was left stationary for about 20 min. When the three-dimensional tissues were in such a condition that they would not flow out, the surgical incision was closed.

Example 6 Chondrogenic Cells Enhance the Expression of Differentiation Markers as a Result of Co-Culturing with Vascular Endothelial Cells Gene expressions in (i) chondrogenic cells cultured in 10 cm easy grip cell culture dish (Falcon) and (ii) chondrogenic cells co-cultured with vascular endothelial cells on gel were analyzed by real time PCR. As a result of co-culturing with vascular endothelial cells, gene expression of the un- or (de-)differentiation marker collagen I decreased (FIG. 15, left panel), and gene expression of cartilage differentiation markers SOX9 and Aggrecan increased (FIG. 15, right panel).

Example 7 In Vitro Long-Term Cultivation

Perichondrocytes (3×10⁶) and vascular endothelial cells (1×10⁶) were co-cultured on Matrigel (BD) in Endothelial Cell Growth Medium SingleQuots Supplements and Growth Factors (EGM) (Lonza) for 2 days to thereby form three-dimensional tissues 4 mm in size. Formation of vasculatures was recognized in the tissues. Subsequently, the cells were cultured further in a growth medium [10% fetal bovine serum (FBS; Gibco), 1% antibiotic antimycotic solution (Sigma)-supplemented Dulbecco's Modified Eagle's Medium Nutrient Mixture F-12 HAM (D-MEM/F-12; Sigma)] or a medium for inducing differentiation into cartilage [10% FBS (Gibco), 1% antibiotic antimycotic solution, L-ascorbic acid 2-phosphate (Wako), dexamethasone (Sigma), insulin growth factor-I (Sigma), basic fibroblast growth factor (Kaken Pharmaceutical)-supplemented D-MEM/F-12 medium (Sigma)] for about 10 days. As a result, regression of vasculatures was confirmed. These three-dimensional tissues could be cultured for a prolonged period of 30 days or more.

Example 8

Freezing Experiments With three-Dimensional Tissues Were Performed by Rapid Freezing With Vitrification in 10% DMSO, 5% Ethylene Glycol and 10% Sucrose-Containing Growth Medium nd vy Slow Freezing with TC protector (Sumitomo Dainippon Pharma)

One week after freezing, tissues were thawed with the growth medium and then suspended in 0.2% collagenase II (Worthington)-containing Dulbecco's modified Eagle medium and Ham's F-12 medium (D-MEM/F-12; Sigma) solution. The resultant suspension was left stationary in an incubator for 20 min and pipetted for separation into single cells. The isolated cell suspension was stained with trypan blue. The number of trypan blue-negative viable cells was determined with an automated cell counter Countess™ (Invitrogen). While 74% cells were viable in the method using DMSO, 88% cells were viable in the method using TC protector. The cells were re-seeded on culture dishes and found to retain a satisfactory proliferative capacity. Further, the thawed tissues retained their shape while they were used in experiments for subcutaneous transplantation into the back of NOD SCID mice (Sankyo Lab.)

Example 9 Examination of Support (FIG. 16)

Methods

A plurality of supports as listed below were gelled and fixed on 24-well plates.
1. Matrigel: either as stock solution or diluted (up to 16-fold dilution)
2. 4-0.5% agarose gel
3. collagen I gel (BD Bioscience)
Cell suspensions of perichondrocytes (2.0×10⁶) and HUVECs (0.6×10⁶) were mixed, centrifuged (950 rpm, 4° C., 5 min) and recovered. The resultant cells were seeded on wells upon which the above-listed supports had been fixed. The cells were then left stationary for 30 min. After addition of 1 ml of EGM, cells were cultured for 3 days.

Results

The results of examination of the requirements that need be satisfied by the supports to be used for preparation of vascularized cartilage are shown in FIG. 16.
A) Examination of Matrigel™ dilution ratios revealed that up to 8-fold dilution can yield vascularized cartilage.
B) When agarose gel was used, formation of vascularized cartilage was not observed under any conditions.
C) When collagen I gel was used, formation of vascularized cartilage was not observed, either.

Example 10 Generation of Human Mature Cartilage by Transplantation of Cryopreserved Vascularized Cartilage (FIG. 17)

Methods

Cryopreservation of Vascularized Cartilage (FIG. 17A)
TC protector was dispensed into tubes for freezing (200-1000 ul/tube). Subsequently, three-dimensional tissues induced in 24-well plates were dipped in and left at 4° C. for several hours to overnight, followed by slow freezing at −80° C.
When rapid freezing (with vitrification) was used, tissues supplemented with 10% DMSO, 5% ethylene glycol and 10% sucrose were dipped in EGM medium for 15-20 min and then transferred to DMEM/F12 (bFGF, IGF, Dex, ascorbic acid, ITS-X, 10% FBS, 1% ABAM) medium (200 μl/tube) supplemented with 2M DMSO, 1M acetamide, 3M propylene glycol. Immediately thereafter, tissues were dipped in liquid nitrogen and preserved in a liquid nitrogen tank.
Thawing of Vascularized Cartilage (FIG. 17B)
Cryopreserved tissues were transferred from −80° C. to a 37° C. water bath. After thawing, tissues were transferred to a 15 ml centrifugal tube and centrifuged (4° C., 750 rpm, 3 min). The resultant supernatant was removed with a Pipetman or the like (aspirator was not used because it would suck in tissues). After PBS wash (5 ml/tube), tissues were re-centrifuged at 4° C., 1500 rpm, for 5 min. After removal of the supernatant (with a Pipetman or the like), tissues were used in transplantation or cultivation experiments.
Subcutaneous Transplantation of Thawed Human Vascularized Cartilage (FIG. 17C)
Six-week-old female NOD/SCID (immunodeficient) mice were purchased from Sankyo Lab. Co., and bred and maintained at Animal Experiment Center, Joint Research Support Section, Advanced Medical Research Center, Yokohama City University. Animal experiments using these mice were performed in accordance with the Yokohama City University Fukuura Campus Animal Experiment Guidelines. The immunodeficient mice were shaved. Skin in the back or face was incised and ablated. The recovered tissues were embedded in the ablated area to perform transplantation.
Removed tissues were fixed in 4% paraformaldehyde (PFA) (Wako)/phosphate buffer (PBS) (pH 7.4) at 4° C. for 2 hr. Then, tissues were washed with 100 mM ammonium chloride (Wako)/PBS at 4° C. for 10 min three times. After soaking in 15% sucrose (Wako)/PBS at 4° C. for 1 hr, tissues were left in 30% sucrose/PBS at 4° C. overnight. Then, the tissues were embedded in O.C.T. Compound (Sakura Japan) (30 ml). After leaving at 4 C.° for 1 hr, the tissues were subjected to rapid freezing with liquid nitrogen to prepare frozen blocks. The resultant frozen blocks were sliced into 5 μm thick sections with cryostat HM 500 O (Zeiss) to prepare frozen tissue sections. The resultant tissue sections were subjected to Alcian blue staining (Muto Pure Chemicals) and Elastica van Gieson staining (Muto Pure Chemicals).

For immunofluorescence staining, frozen blocks were sliced into 5 μm thick sections with cryostat HM 500 O (Zeiss) to prepare frozen tissue sections. The resultant tissue sections were washed with 0.1% tween TBS to remove O.C.T. Compound. TBS-T around the frozen sections was wiped out. The targets of staining were marked with a water-repellent pen (Dako) in an enclosing manner to make them water-repellent. Subsequently, the tissues were blocked with Protein Block Serum-Free Ready-to-Use (Dako) at 4° C. for 24 hr. Primary antibodies were reacted at 4° C. overnight. After this treatment, resultant tissues were washed with TBS-T for 5 min three times. Secondary antibodies were added dropwise and reacted at room temperature for 2 hr. After washing with TBS-T for 5 min three times, nuclear staining and inclusion were performed with DAPI-supplemented FA Mounting Fluid (Becton Dickinson). For dilution of the primary and secondary antibodies, Protein Block Serum-Free Ready-to-Use (DAKO) was used.

Results

FIG. 17A shows the processes of cryopreserving vascularized cartilage. Left panel: Tissues formed in a culture dish. Center panel: Tissues recovered with a spatula. Right panel: The recovered tissues as dipped in cryopreservation solvent (TC protector) immediately before freezing. FIG. 17B shows gross observation of human vascularized cartilage thawed one month after freezing. FIG. 17C shows histological analysis of subcutaneously transplanted sample of thawed human vascularized cartilage. Histological analysis of the sample subcutaneously transplanted into the back of immunodeficient mice revealed that the transplanted human vascularized cartilage reconstructed cartilage tissues comprising cartilage matrix stained by Alcian blue and collagen II antibody.

Example 11 Long-Term Cultivation of Vascularized Cartilage (FIGS. 18 & 19)

Methods

EGM and Matrigel (150 μm each) were added separately to 24-well plates, which were then left stationary in an incubator for 30 min. Cell suspensions of perichondrocytes ($2.0 \times 10^6$ cells/ml) and HUVEC ($0.6 \times 10^6$ cells/ml) were mixed and centrifuged (950 rpm, 4° C., 5 min). Recovered cells were seeded on the wells. After the cells were left stationary for 30 min, 1 mL of EGM was added. Then, cells were cultured for 3 days. Induced three-dimensional tissues were seeded on culture vessels and subjected to rotary culture with an RWV bioreactor (Synthecon) using a three-dimensional culture medium for differentiation into cartilage (DMEM/F12, dexamethasone, ascorbic acid 2-phosphate, bFGF, IGF-1, ITS-X, 1% antibiotic antimycotic solution) in an incubator whose gas phase condition had been set at 37° C. and a $CO_2$ concentration of 5%. The rotation rate was adjusted to 7-12 rpm. After 60 days of culture for differentiation into cartilage, cell masses 5 mm to 1 cm in size were recovered. The mechanical strength of these cell masses was confirmed by applying manual pressure with tweezers or the like. After they were confirmed to have sufficient strength, cell masses were transplanted into the head of immunodeficient mice.

Results

FIG. 18 shows histological analysis of long-term cultured vascularized cartilage. Upon culturing the prepared vascularized cartilage for a period as long as 60 days, both a blood vessel-containing perichondral tissue and a blood vessel-free cartilage tissue were shown to have formed. Upper left panel: macroscopic image of the formed tissues. Upper right panel: immunostaining showed that the central part expressed the cartilage marker aggrecan, with laminin surrounding the central part. Lower left panel: enlarged image of immunostaining Lower center panel: HE staining. Lower right panel: Alcian Blue staining. The induced three-dimensional tissue had such a high mechanical strength that it was not destroyed even when it was manually compressed with tweezers.

FIG. 19 shows transplantation of mature cartilage derived from long-term cultured vascularized cartilage. Long-term cultured vascularized cartilage (shown in a small window at the lower left corner of the upper left panel) was transplanted into a facial site and found to have a sufficient mechanical strength to withstand subcutaneous tension. Upper and lower photographs were taken to confirm the raised portion as viewed from different angles.

All publications, patents and patent applications cited herein are incorporated herein by reference in their entirety.

INDUSTRIAL APPLICABILITY

The present invention has potential applications including regenerative therapy, drug screening, and preparation of matrixes produced by chondrocytes.

The invention claimed is:

1. A method for forming chondrocyte tissue in an animal, said method comprising:
    (1) inducing the formation of three-dimensional tissue with vasculature in a self-drive manner by co-culturing chondrogenic cells with vascular cells on a substrate in vitro; and
    (2) implanting the three-dimensional tissue formed in step (1) into an animal causing an at least partial regression of the vasculature and in vivo maturation into a chondrocyte tissue,
    wherein the substrate has a hardness of 0.5-25 kPA or the substrate is a plate having a shape in which cells gather in the bottom, and wherein the chondrogenic cells and vascular cells are co-cultured at a mixing ratio of 1:0.3-1.

2. The method according to claim 1, wherein the chondrogenic cells amplify as a result of co-culture with vascular cells.

3. The method according to claim 1, wherein the formation of three-dimensional tissue in a self-drive manner is induced by co-culturing chondrogenic cells with vascular cells on the substrate.

4. The method according to claim 1, wherein the chondrogenic cells are co-cultured with vascular cells in the presence of at least one component selected from the group consisting of fibroblast growth factor 2 (bFGF (FGF2)), fibroblast growth factor 4 (FGF4), fibroblast growth factor 5 (FGF5), bone morphogenetic protein 2 (BMP2), bone morphogenetic protein 3 (BMP3), bone morphogenetic protein 4 (BMP4), bone morphogenetic protein 6 (BMP6), connective tissue growth factor (CTGF), transforming growth factor β1 (TGF-β1), transforming growth factor β2 (TGF-β2), transforming growth factor β3 (TGF-(β3), insulin-like growth factor 1 (IGF-1), hepatocyte growth factor (HGF), aggrecan, hyaluronic acid, endothelial cell growth factor (ECGF), endothelial cell growth supplement (ECGS), endothelial cell-derived growth factor (ECDGF), epidermal growth factor (EGF), acidic fibroblast growth factor (acidic FGF), macrophage-derived growth factor (MDGF), platelet-derived growth factor (PDGF), tumor angiogenesis factor (TAF), vascular endothelial growth factor (VEGF), bovine brain extract (BBE), bovine pituitary extract (BPE), glucocorticoid, cholesterol, and vitamins.

5. The method according to claim 1, wherein the chondrogenic cell is any one of chondrocyte, immature chondrocyte, cartilage progenitor cell or cartilage stem cell.

6. The method according to claim 5, wherein the chondrocyte has been obtained from a tissue selected from the group consisting of rib cartilage, nasal cartilage, ear cartilage, tracheal cartilage, pharyngeal cartilage, thyroid cartilage, arytenoid cartilage, cricoid cartilage, tendon, ligament, interarticular cartilage, and intervertebral disc.

7. The method according to claim 5, wherein the immature chondrocyte, the cartilage progenitor cell or the cartilage stem cell has been obtained from a tissue selected from the group consisting of cartilage, perichondrium, bone marrow, placenta, umbilical cord, skin, muscle, fat, and periosteum.

8. The method according to claim 1, wherein the chondrogenic cell and the vascular cell are derived from the same individual.

9. The method according to claim 1, wherein the chondrogenic cell and the vascular cell are derived from different individuals.

10. A method for forming chondrocyte tissue, said method comprising:
   (1) inducing the formation of three-dimensional tissue with vasculature in a self-drive manner by co-culturing chondrogenic cells with vascular cells on a substrate in vitro; and
   (2) further culturing in vitro the three-dimensional tissue formed in step (1) causing an at least partial regression of the vasculature and maturation into a chondrocyte tissue,
   wherein the substrate has a hardness of 0.5-25 kPA or the substrate is a plate having a shape in which cells gather in the bottom, and wherein the chondrogenic cells and vascular cells are co-cultured at a mixing ratio of 1:0.3-1.

11. The method according to claim 10, wherein the chondrogenic cells amplify as a result of co-culture with vascular cells.

12. The method according to claim 10, wherein the formation of three-dimensional tissue in a self-drive manner is induced by co-culturing chondrogenic cells with vascular cells on the substrate.

13. The method according to claim 10, wherein the chondrogenic cells are co-cultured with vascular cells in the presence of at least one component selected from the group consisting of fibroblast growth factor 2 (bFGF (FGF2)), fibroblast growth factor 4 (FGF4), fibroblast growth factor 5 (FGF5), bone morphogenetic protein 2 (BMP2), bone morphogenetic protein 3 (BMP3), bone morphogenetic protein 4 (BMP4), bone morphogenetic protein 6 (BMP6), connective tissue growth factor (CTGF), transforming growth factor β1 (TGF-β1), transforming growth factor β2 (TGF-β2), transforming growth factor β3 (TGF-β3), insulin-like growth factor 1 (IGF-1), hepatocyte growth factor (HGF), aggrecan, hyaluronic acid, endothelial cell growth factor (ECGF), endothelial cell growth supplement (ECGS), endothelial cell-derived growth factor (ECDGF), epidermal growth factor (EGF), acidic fibroblast growth factor (acidic FGF), macrophage-derived growth factor (MDGF), platelet-derived growth factor (PDGF), tumor angiogenesis factor (TAF), vascular endothelial growth factor (VEGF), bovine brain extract (BBE), bovine pituitary extract (BPE), glucocorticoid, cholesterol, and vitamins.

14. The method according to claim 10, wherein the chondrogenic cell is any one of chondrocyte, immature chondrocyte, cartilage progenitor cell or cartilage stem cell.

15. The method according to claim 14, wherein the chondrocyte has been obtained from a tissue selected from the group consisting of rib cartilage, nasal cartilage, ear cartilage, tracheal cartilage, pharyngeal cartilage, thyroid cartilage, arytenoid cartilage, cricoid cartilage, tendon, ligament, interarticular cartilage, and intervertebral disc.

16. The method according to claim 14, wherein the immature chondrocyte, the cartilage progenitor cell or the cartilage stem cell has been obtained from a tissue selected from the group consisting of cartilage, perichondrium, bone marrow, placenta, umbilical cord, skin, muscle, fat, and periosteum.

17. The method according to claim 10, wherein the chondrogenic cell and the vascular cell are derived from the same individual.

18. The method according to claim 10, wherein the chondrogenic cell and the vascular cell are derived from different individuals.

19. A method of screening for drugs effective as pharmaceuticals, comprising contacting a drug to be screened with a chondrocyte tissue in an animal, wherein said chondrocyte tissue in said animal is prepared by the method of claim 1.

20. A method of screening for drugs effective as pharmaceuticals, comprising contacting a drug to be screened with a chondrocyte tissue, wherein said chondrocyte tissue is prepared by the method of claim 10.

* * * * *